(12) United States Patent
Rosario et al.

(10) Patent No.: US 11,389,533 B2
(45) Date of Patent: Jul. 19, 2022

(54) METHOD OF TREATING INFLAMMATORY BOWEL DISEASE

(71) Applicant: Millennium Pharmaceuticals, Inc., Cambridge, MA (US)

(72) Inventors: Maria Rosario, Mystic, CT (US); Morris Barocas, Deerfield, IL (US); Marc R. Gastonguay, Tariffville, CT (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/309,002

(22) PCT Filed: Jun. 12, 2017

(86) PCT No.: PCT/US2017/037072
§ 371 (c)(1),
(2) Date: Dec. 11, 2018

(87) PCT Pub. No.: WO2017/218434
PCT Pub. Date: Dec. 21, 2017

(65) Prior Publication Data
US 2019/0255172 A1 Aug. 22, 2019

Related U.S. Application Data

(60) Provisional application No. 62/349,026, filed on Jun. 12, 2016.

(51) Int. Cl.
| | | |
|---|---|---|
| *A61K 39/00* | (2006.01) | |
| *A61K 39/395* | (2006.01) | |
| *C07K 16/28* | (2006.01) | |

(52) U.S. Cl.
CPC ........ *A61K 39/395* (2013.01); *C07K 16/2839* (2013.01); *A61K 2039/505* (2013.01); *A61K 2039/545* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 7,147,851 B1 | 12/2006 | Ponath et al. |
| 7,402,410 B2 | 7/2008 | Ponath et al. |
| 9,663,579 B2 | 5/2017 | Fox et al. |
| 9,764,033 B2 | 9/2017 | Diluzio et al. |
| 10,004,808 B2 | 6/2018 | Fox et al. |
| 10,040,855 B2 | 8/2018 | Diluzio et al. |
| 10,143,752 B2 | 12/2018 | Fox et al. |

FOREIGN PATENT DOCUMENTS

| | | |
|---|---|---|
| WO | 96/24673 A1 | 8/1996 |
| WO | 98/06248 A2 | 5/1998 |
| WO | 31/078779 A2 | 7/2002 |
| WO | 2007/061679 A1 | 5/2007 |
| WO | 2012/151247 A2 | 2/2013 |
| WO | 2012/151248 A2 | 2/2013 |
| WO | 2016/086147 A1 | 6/2016 |
| WO | 2016/105572 A1 | 6/2016 |
| WO | 2016/144720 A1 | 9/2016 |
| WO | 2016/200880 A1 | 12/2016 |
| WO | 2017/160700 A1 | 9/2017 |
| WO | 2017/165742 A1 | 9/2017 |
| WO | 2017/165778 A1 | 9/2017 |
| WO | 2017/160699 A2 | 11/2017 |
| WO | 2017/192867 A1 | 11/2017 |

OTHER PUBLICATIONS

Khanna et al. Therapeutic Drug Monitoring of TNF Antagonists in Inflammatory Bowel Disease. Gastroenterology & Hepatology vol. 10(8):478-489, Aug. 2014. (Year: 2014).*
Rosario et al. Relationship Between Vedolizumab Pharmacokinetics and Endoscopic Outcomes of Patients With Ulcerative Colitis. 2014 Advances in Inflammatory Bowel Diseases, Dec. 4-6, 2014; Abstract O-003. (Year: 2014).*
Feagan et al. Vedolizumab as Induction and Maintenance Therapy for Ulcerative Colitis. N Engl J Med 369;8, pp. 702-710, Aug. 22, 2013 and supplement pp. 1-47 (Year: 2013).*
125476Orig1s000. Clinical Pharmacology and Biopharmaceutics Review(s). Center for Drug Evaluation and Research, pp. 1-158, Apr. 3, 2014 (Year: 2014).*
Meeting News Coverage: Ulcerative Colitis Resource Center. Increased vedolizumab dosing frequency improved remission in IBD patients who lost response, pp. 1-2, Dec. 18, 2014.(Year: 2014).*
European Medicines Agency, International non-proprietary name: vedolizumab. pp. 1-166, Mar. 20, 2014 (Year: 2014).*
Ladd et al. Dose Escalation of Vedolizumab From Every 8 Weeks to Every 4 or 6 Weeks Enables Patients With Inflammatory Bowel Disease to Recapture Response. Gastroenterology, 150(4), Supplement 1, pp. S235-S236, Abstact: Sa1086, Apr. 2016. (Year: 2016).*
McKnight W., Faster clearance of vedolizumab associated with less mucosal healing in UC. Conference Coverage, p. 1-3, Dec. 15, 2014. (Year: 2014).*
Sands et al. Effects of Increased Vedolizumab Dosing Frequency on Clinical Remission and Response in Ulcerative Colitis and Crohn's Disease. Inflammatory Bowel Diseases, vol. 20, Issue suppl_1, Dec. 1, 2014, p. S67. (Year: 2014).*
International Search Report and Written Opinion dated Oct. 6, 2017 in International (PCT) Application No. PCT/US2017/037072 (21 pages).

(Continued)

*Primary Examiner* — Maher M Haddad
(74) *Attorney, Agent, or Firm* — Womble Bond Dickinson (US) LLP

(57) ABSTRACT

The invention provides methods for identifying patients who do not adequately respond to vedolizumab therapy and treating these patients with a personalized treatment approach using vedolizumab.

44 Claims, 1 Drawing Sheet
Specification includes a Sequence Listing.

(56) References Cited

OTHER PUBLICATIONS

Feagan, Brian G., et al. "Vedolizumab as induction and maintenance therapy for ulcerative colitis." New England Journal of Medicine, vol. 369, No. 8, pp. 699-710, Aug. 22, 2013.
McLean, Leon P., et al. "Pharmacodynamic assessment of vedolizumab for the treatment of ulcerative colitis." Expert opinion on drug metabolism & toxicology, vol. 12, No. 7, pp. 833-842, May 12, 2016.
Rosario, M., et al. "Population pharmacokinetics-pharmacodynamics of vedolizumab in patients with ulcerative colitis and Crohn's disease." Alimentary Pharmacology & Therapeutics, vol. 42, No. 2, pp. 188-202, May 20, 2015.
Sands, Bruce, et al. "P-098 Effects of Increased Vedolizumab Dosing Frequency on Clinical Remission and Response in Ulcerative Colitis and Crohn's Disease." Inflammatory Bowel Diseases, vol. 20, No. suppl_1, p. S67, Dec. 1, 2014.
TGA "AusPAR Attachment 2 Extract from the Clinical Evaluation Report for Vedolizumab (rch)" Proprietary Product Name: Entyvio/Kynteles Sponsor: Takeda Pharmaceuticals Australia Pty Ltd., Feb. 12, 2014, Retrieved from URL: https://www.tga.gov.au/sites/default/files/auspar-vedolizumab-141117-cer.pdf.
"Takeda Initiates Two Phase III Studies with Vedolizumab (MLN0002) in Patients with Inflammatory Bowel Disease-Simultaneous Studies to Investigate Novel Therapy for Ulcerative Colitis and Crohn's Disease," 2 pages, Jan. 22, 2009.
ClinicalTrials.gov Archive. NCT03029143. Vedolizumab Intravenous (IV) Dose Optimization in Ulcerative Colitis (ENTERPRET). Study Record Version Jan. 20, 2017.
ClinicalTrials.gov Archive. Study of Vedolizumab (MLN0002) in Patients With Moderate to Severe Ulcerative Colitis. NCT00783718, Nov. 2, 2008, pp. 1-3.
ClinicalTrials.gov—NCT 00790933 on Nov. 14, 2008 [cited Apr. 12, 2018], An Open-label Study of Vedolizumab (MLN0002) in Participants With Ulcerative Colitis and Crohn's Disease (GEMINI LTS).
ClinicalTrials.org NCT00783692 on Mar. 18, 2011, "Study of Vedolizumab in (MLN002) in Patients with Moderate to Severe Crohn's Disease".
ClinicalTrials.org NCT01224171 on Dec. 22, 2010, "Study of Vedlizumab in Patients with Moderate to Severe Crohn's Disease".
Cunliffe et al., "Review Article: Monitoring for Drug Side-Effects in Inflammatory Bowel Disease," Aliment Pharmacol Ther., 16:647-662 (2002).
Dignass, A.U., "New Developments in the Management of Steroid-refractory Inflammatory Bowel Disease," Business Briefing: European Gastroenterology Review, 2005, pp. 1-5.
E.V. Loftus, "New Data on the Use of Biologic Agents for Crohn's Disease and Ulcerative Colitis: Highlights from the 2009 CCFA Advances in IBD Meeting," Gastroenterology & Hepatology, vol. 6, Issue 2, Supplement 3, (2010).
Feagan et al, "A randomized Controlled Trial of a Humanized .alpha.4.beta.7 Antibody in Ulcerative Colitis (UC)," Am J Gastroenterol, 98(9s):S248-S249. Abstract 749 (2003).
Feagan et al., "Efficacy and Safety of a Humanized .alpha.4.beta.7 Antibody in Active Crohn's Disease (CD). Gastroenterology," 124(4)(suppl 1):A25-A26. Abstract 178 (2003).
Feagan et al. "Emerging Safety Profile of Vedolizumab: A Novel, Selective Integrin Inhibitor for Treatment of IBD," J Crohn's Colitis, 4(suppl 1) Abstract P149 (2010).

Feagan et al., "An Ascending Dose Trial of a Humanized A. sub 4B.sub.7 Antibody in Ulcerative Colitis(US)," Gastroenterol. ,118(4):A874, (Abstract No. 4851), (2000).
Feagan et al., "Emerging Safety Profile of Vedolizumab: A Novel, Selective Integrin Inhibitor for Treatment of IBD," P149 poster (2010).
Feagan, et al., "Emerging Safety Profile of Vedolizumab: A Novel, Selective Integrin Inhibitor for the Treatment of IBD," 15(S2): S12, Abstract P-0025, 2009 IBD Abstracts (2009).
Fedyk et al, "The Pharmacologic and Toxicologic Profile of the Gastrointestinal-Selective, Anti-Inflammatory Drug Vedolizumab in Cynomolgus Macaques," presentation (2010).
Gordon et al., "Randomised Double-Blind Placebo-Controlled Trial of Recombinant Humanised Antibody to .alpha.4 Integrin (AntegrenTM) in Active Crohn's Disease." Gastroenterology, 116(4) Part 2:A726 (1999).
Katz, "Update in Medical Therapy in Inflammatory Bowel Disease: A Clinician's View," Digestive Diseases, 17:163-171 (1999).
Kornbluth et al. "Ulcerative Colitis Practice Guidelines in Adults: American College of Gastroenterology, Practice Parameters Committee," Am. J. Gastroenterol. 105(3): 501-23 (2010).
Marehbian et al., Adverse Events Associated with Common Therapy Regimens for Moderate-to-Severe Crohn's Disease, The American Journal of Gastroenterology, 104:2524-2533 (2009).
Mayo Clinic Staff, Inflammatory Bowel Disease (IBD) Treatments and Drugs—Mayo Clinic, <http://www.mayoclinic.org/diseases-conditions/inflammatory-bowel-disease/-> basics/treatments.con-20034908, pp. 1-2, May 26, 2015.
Moss et al. Residual Inflammation and Ulcerative Colitis in Remission. Gastroenterology & Hepatology vol. 10, Issue 3 Mar. 2014, pp. 181-182 (Year: 2014).
Okayasu et al., "A Novel Method in the Induction of Reliable Experimental Acute and Chronic Ulcerative Colitis in Mice," Gastroenterology, 98:594-702 (1990).
Parikh et al., "Long-Term Clinical Experience with Vedolizumab for the Treatment of Inflammatory Bowel Disease: A Phase 2 Open-Label Safety Extension Study," J Crohn's Colitis, 5(1):S123, Abstract P263 (2011).
Parikh et al., "Long-Term Clinical Experience with Vedolizumab for the Treatment of Inflammatory Bowel Disease: A Phase 2 Open-Label Safety Extension Study," P263 poster (2011).
Parikh et al., "Long-Term Clinical Experience with Vedolizumab for the Treatment of Inflammatory Bowel Disease Results of a Phase 2 Open-Label Safety Extension Study," Inflamm Bowel Disease, 17(suppl S1):S56. Abstract P-146 (2011).
Parikh et al., "Long-Term Clinical Experience with Vedolizumab for the Treatment of Inflammatory Bowel Disease Results of a Phase 2 Open-Label Safety Extension Study," P-146 poster (2011).
Parikh et al., "Vedolizumab for the Treatment of Active Ulcerative Colitis: A Randomized Conrolled Phase 2 Dose-ranging Study," Inflamm. Bowel Dis., 18(8):1470-1479 (2012).
Pastorelli et al., Emerging drugs for the treatment of ulcerative colitis. Expert Opin Emerg Drugs. Sep. 2009 ; 14(3): 505-521.
Sandborn et al., "Vedolizumab as Induction and Maintance Therapy for Crohn's Disease,"The New England Journal of Medicine, 369(8):711-721 (Aug. 22, 2013).
Scholz C, Wyant T, Leach T, Sankoh S, Mould DR, Patella M, et al, Clinical pharmacology of vedolizumab (MLN0002) in patients with active ulcerative colitis. P164 poster (2009).
Scholz et al., "Clinical Pharmacology of Vedolizumab (MLN0002) in Patients with Active Ulcerative Colitis," ECCO Annual Meeting Hamburg, Germany Feb. 5, 2009.

\* cited by examiner

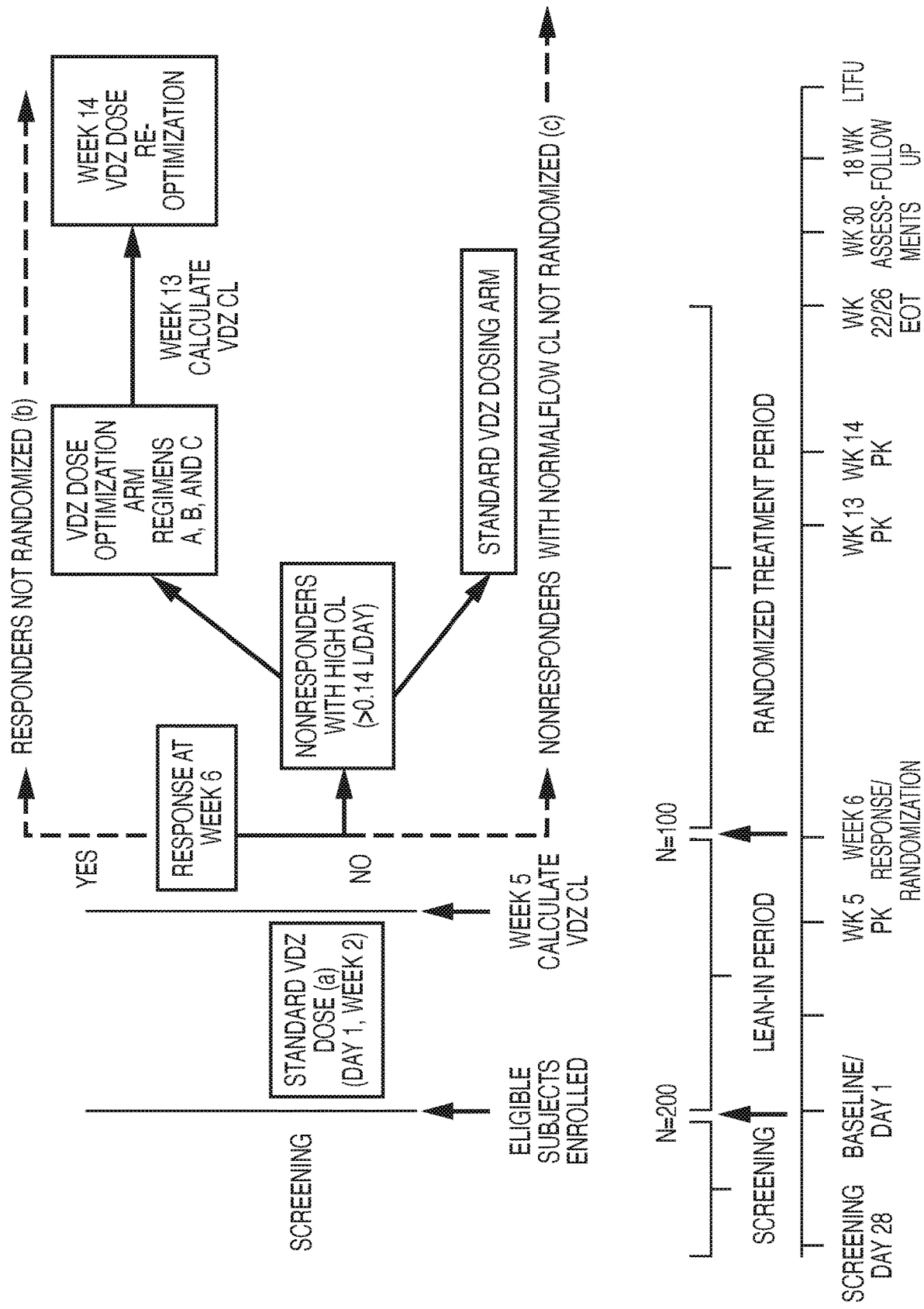

SEQUENCE LISTING

<160> NUMBER OF SEQ ID NOS: 11

<210> SEQ ID NO 1
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Gly Ser Gly Tyr Thr Phe
        35                  40                  45

Thr Ser Tyr Trp Met His Trp Val Arg Gln Ala Pro Gly Gln Arg Leu

```
            50                  55                  60
Glu Trp Ile Gly Glu Ile Asp Pro Ser Glu Ser Asn Thr Asn Tyr Asn
 65                  70                  75                  80

Gln Lys Phe Lys Gly Arg Val Thr Leu Thr Val Asp Ile Ser Ala Ser
                 85                  90                  95

Thr Ala Tyr Met Glu Leu Ser Ser Leu Arg Ser Glu Asp Thr Ala Val
                100                 105                 110

Tyr Tyr Cys Ala Arg Gly Gly Tyr Asp Gly Trp Asp Tyr Ala Ile Asp
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Ala Gly Ala Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465                 470
```

<210> SEQ ID NO 2
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
                20                  25                  30

Thr Pro Gly Glu Pro Ala Ser Ile Ser Cys Arg Ser Ser Gln Ser Leu
            35                  40                  45

Ala Lys Ser Tyr Gly Asn Thr Tyr Leu Ser Trp Tyr Leu Gln Lys Pro
        50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 3
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
                20                  25                  30

Tyr Gly Asn Thr Tyr Leu Ser Trp Tyr Leu Gln Lys Pro Gly Gln Ser
            35                  40                  45

```
Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

```
<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Tyr Trp Met His
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Ile Asp Pro Ser Glu Ser Asn Thr Asn Tyr Asn Gln Lys Phe Lys
1               5                   10                  15

Gly

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Tyr Asp Gly Trp Asp Tyr Ala Ile Asp Tyr
1               5                   10
```

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ser Ser Gln Ser Leu Ala Lys Ser Tyr Gly Asn Thr Tyr Leu Ser
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Gln Gly Thr His Gln Pro Tyr Thr
1               5

<210> SEQ ID NO 10
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Lys Val Glu Ile Lys
            100                 105                 110

```
<210> SEQ ID NO 11
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
            115
```

METHOD OF TREATING INFLAMMATORY BOWEL DISEASE

RELATED APPLICATIONS

This application is a United States National Phase under 35 U.S.C. § 371 of International Application No. PCT/US2017/037072, filed on Jun. 12, 2017, which claims priority to, and the benefit of U.S. Provisional Application No. 62/349,026 filed on Jun. 12, 2016. The entire contents of the foregoing applications are hereby incorporated by reference.

SEQUENCE LISTING

The instant application contains a Sequence Listing, which has been submitted electronically in ASCII format and is hereby incorporated by reference in its entirety. Said ASCII copy, created on Jun. 23, 2017, is named 079259-0878_SEQLIST.txt and is 12.2 kb in size.

BACKGROUND

Inflammatory bowel disease (IBD), such as ulcerative colitis and Crohn's disease, for example, can be a debilitating and progressive disease involving inflammation of the gastrointestinal tract. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *New Engl. J. Med.*, 325:928-937 (1991) and Podolsky, *New Engl. J. Med.*, 325:1008-1016 (1991). As the disease progresses, treatment progresses into regimens that expose patients to progressive risk of side effects and loss of quality of life.

Integrin receptors are important for regulating both lymphocyte recirculation and recruitment to sites of inflammation (Carlos, T. M. and Harlan, J. M., *Blood*, 84:2068-2101 (1994)). The human α4β7 integrin has several ligands, one of which is the mucosal vascular addressin MAdCAM-1 (Berlin, C., et al., *Cell* 74: 185-195 (1993); Erle, D. J., et al., *J. Immunol.* 153:517-528 (1994)), which is expressed on high endothelial venules in mesenteric lymph nodes and Peyer's patches (Streeter, P. R., et al., *Nature* 331:41-46 (1998)). As such, the α4β7 integrin acts as a homing receptor that mediates lymphocyte migration to intestinal mucosal lymphoid tissue (Schweighoffer, T., et al., *J. Immunol.* 151: 717-729 (1993)).

Antibodies against human α4β7 integrin, such as murine monoclonal antibody Act-1 (mAb Act-1), interfere with α4β7 integrin binding to mucosal addressin cell adhesion molecule-1 (MAdCAM-1) present on high endothelial venules in mucosal lymph nodes. Act-1 was originally isolated by Lazarovits, A. I., et al., *J. Immunol.* 133:1857-1862 (1984), from mice immunized with human tetanus toxoid-specific T lymphocytes and was reported to be a mouse IgG1/κ antibody. Subsequent analysis of the antibody by Schweighoffer, T., et al., *J. Immunol.* 151:717-729 (1993) demonstrated that it can bind to a subset of human memory CD4+ T lymphocytes which selectively express the α4β7 integrin. Entyvio™ vedolizumab, an anti-α4β7 integrin monoclonal antibody (mAb) with structural features derived from Act-1, is indicated for treating ulcerative colitis (UC) and Crohn's disease (CD). Studies reporting the activity of vedolizumab in treating these disorders (Feagen et al. *NEJM* 369:699-710 (2013) and Sandborn et al. *NEJM* 369:711-721 (2013)) showed varying levels of success depending on the disorder and nature of prior therapies. As these were lengthy studies and there are a growing number of treatment options available to patients, there is a need to identify patients who can benefit from modified vedolizumab therapy early in their treatment. Expedient and accurate treatment decisions lead to effective management of the disease.

SUMMARY OF THE INVENTION

The invention relates to the identification and treatment of patients who do not initially respond adequately to therapy comprising an anti-α4β7 antibody, such as vedolizumab. Early in the course of treatment, e.g., after one or two doses of vedolizumab, factors measured from the patient or from biological samples of the patient indicate whether a patient should receive personalized treatment approach.

In one aspect, pharmacokinetics or pharmacodynamics factors can indicate whether a patient should receive modified treatment with an anti-α4β7 antibody, such as vedolizumab. As higher therapeutic mAb trough concentrations have been associated with greater efficacy, understanding determinants of mAb clearance may optimize dosing regimens. Applicants have identified a subset of inflammatory bowel disease patients who do not adequately respond to conventional treatment with an anti-α4β7 antibody, such as vedolizumab, and have identified a modified dosing regimen to be administered after clinically relevant determinants of anti-α4β7 antibody, such as antibody concentration, body weight, and albumin levels, are recognized.

In some embodiments, a pharmacokinetics factor is serum concentration of the anti-α4β7 antibody. In some embodiments, a pharmacokinetics factor is mean serum trough concentration. In other embodiments, a pharmacokinetics factor is therapeutic antibody clearance. Higher doses are projected to produce higher exposure levels and may result in efficacy in subjects who have high vedolizumab clearance, based on a Week 5 serum vedolizumab concentration threshold (<50 μg/mL). In addition, if subsequent $C_{trough}$ levels exceed the exposure limit of 90 μg/mL, subsequent doses may be a decreased amount.

In some embodiments, methods described herein comprise measuring albumin concentration, e.g., a serum albumin concentration. An albumin concentration less than 3.2 g/dL further identifies the patient as a non-responder of an anti-α4β7 antibody, e.g., vedolizumab. The albumin concentration can be less than 3.0 g/dL, less than 2.0 g/dL, or less than 1.7 g/dL, in the range of 0.0 to 3.1 g/dL, in the range of 1.0 to 3.0 g/dL, in the range of 0.5 to 3.2 g/dL, or in the range of 2.0 to 3.1 g/dL.

In one aspect, the invention relates to a method for identifying a patient as a candidate for personalized treatment, the method comprising the steps of: measuring the clearance of vedolizumab in a biological sample obtained from a patient suffering from inflammatory bowel disease (IBD) and who was administered at least two doses of vedolizumab within the previous four months; and identifying the patient for continued treatment with vedolizumab if the clearance in the patient is greater than 0.14 L/day. The clearance may be greater than 0.20 L/day or between 0.14 and 0.4 L/day.

In another aspect, the invention relates to a method for identifying a patient as a candidate for personalized treatment, the method comprising the steps of: measuring the clearance of vedolizumab in a biological sample obtained from a patient suffering from inflammatory bowel disease (IBD) and who was administered at least one dose of vedolizumab within the previous two months; and identifying the patient for continued treatment with vedolizumab if the clearance in the patient is greater than 0.14 L/day. The clearance may be greater than 0.20 L/day or between 0.14 and 0.24 L/day. In some embodiments, the patient was administered at least one dose of vedolizumab within the previous month. In some embodiments, the patient was administered at least two doses of vedolizumab within the previous month.

The invention further relates to assays for use in measuring the factors described herein for identifying a patient who is a candidate for personalized treatment to an anti-α4β7 antibody, such as vedolizumab. In some embodiments the assay is a pharmacokinetic assay for circulating anti-α4β7 antibody. In an embodiment, the assay may measure low or sustained positive levels of anti-α4β7 antibody, such as less than 13, 12, 11, 10, 9, 8, 7, 6, 5, 4, 3, 2, or 1 μg per ml in a serum sample from a patient, e.g., for predicting the ability to respond or maintain a response or remission of the IBD afflicting the patient. In an embodiment, the serum concentration of the anti-α4β7 antibody may be measured by a sandwich ELISA assay. In an embodiment, the serum concentration of the anti-α4β7 antibody may be measured in an antibody bridging assay.

In one aspect, a method for treating a human patient having inflammatory bowel disease (IBD), the method comprises: selecting a human patient having IBD and having a serum concentration of vedolizumab which is less than 13 μg per ml at a time point that is three or four weeks after a second dose of vedolizumab, wherein a first dose of vedolizumab was administered to the subject two weeks prior to the second dose of vedolizumab; and administering vedolizumab to the human patient having IBD, thereby treating the human patient having IBD. In one embodiment, the first and second dose of vedolizumab comprises 300 mg. In one embodiment, the third dose of vedolizumab comprises 600 mg and all subsequent doses comprise 300 mg. In one embodiment, the third and subsequent doses of vedolizumab comprise 600 mg. In one embodiment, the patient received the first and the second dose intravenously. In some embodiments, the third and subsequent doses of vedolizumab are at 4 week intervals. In some embodiments, the patient had an inadequate response with, lost response to, or was intolerant to a TNF blocker.

One embodiment provided herein is an in vitro method for identifying a vedolizumab non-responder having Inflammatory Bowel Disease (IBD) to treatment with vedolizumab, the method comprising measuring the concentration of vedolizumab in a blood sample from the patient by contacting the blood sample with an anti-vedolizumab antibody, wherein the sample is obtained about three or four weeks following administration of a second dose of vedolizumab, wherein a first dose of vedolizumab was administered to the subject two weeks prior to the second dose of vedolizumab, and wherein a vedolizumab concentration of less than 13 μg per ml in the blood sample indicates that the patient is not responsive to treatment with vedolizumab. In one embodiment, the method further comprises administering vedolizumab to the patient. In one embodiment, the first and second dose of vedolizumab comprises 300 mg. In one embodiment, the third dose of vedolizumab comprises 600 mg. In one embodiment, the patient received the first and the second dose intravenously. In some embodiments, the patient had an inadequate response with, lost response to, or was intolerant to a TNF blocker.

BRIEF DESCRIPTION OF THE DRAWINGS

FIG. 1 shows a schematic of study design. On Day 1 and Week 2 (Lead-in Period), all eligible subjects will receive vedolizumab IV 300 mg.[a] Subjects who respond at Week 6 (by partial Mayo score) will not be randomized and will receive appropriate treatment per physician discretion. Following the last dose of study drug, subjects will have the 18-week Follow-Up Safety Visit and 6 month long-term follow-up (LTFU) telephone call.[b] Subjects who are non-responders at Week 6 and have normal to low vedolizumab clearance (≤0.14 L/day) will not be randomized and will receive appropriate treatment per physician discretion. Following the last dose of study drug, subjects will have the 18-week Follow-Up Safety Visit and 6 month LTFU telephone call.[c]

DETAILED DESCRIPTION

The invention relates to methods for treating with an anti-α4β7 antibody, e.g., vedolizumab, a patient having inflammatory bowel disease (IBD), methods for identifying a patient for modified treatment with the antibody, such as vedolizumab, and methods for maintaining remission of IBD in a patient.

Not all patients with inflammatory bowel diseases who receive treatment with an anti-α4β7 antibody, such as vedolizumab, respond to the treatment and some do not respond fully to treatment. Due to the morbidity of these diseases, there is a need to quickly identify those patients who do not adequately respond to anti-α4β7 antibody therapy and adjust their dosage regimen to improve efficacy outcomes. This application relates to the surprising discovery that higher induction exposure of the anti-α4β7 antibody is associated with improved efficacy outcomes in inflammatory bowel disease patients (e.g., ulcerative colitis patients).

Vedolizumab, a humanized monoclonal antibody that binds specifically to the $\alpha_4\beta_7$ integrin, is indicated for the treatment of patients with moderately to severely active ulcerative colitis (UC) and Crohn's disease (CD). Vedolizumab has a novel gut-selective mechanism of action that differs from that of other currently marketed biologic agents for the treatment for inflammatory bowel disease (IBD), including natalizumab and tumor necrosis factor-α (TNF-α) antagonists. By binding to cell surface-expressed $\alpha_4\beta_7$, vedolizumab blocks the interaction of a subset of memory gut-homing T lymphocytes with mucosal addressin cell adhesion molecule-1 (MAdCAM-1) expressed on endothelial cells. Consequently, migration of these cells into inflamed intestinal tissue is inhibited.

The pharmacokinetics of other therapeutic monoclonal antibodies used for the treatment of UC and CD has been previously reported. Several factors are associated with accelerated clearance of these antibodies including the presence of anti-drug antibodies, sex, body size, concomitant immunosuppressant use, disease type, albumin concentration, and degree of systemic inflammation. Furthermore, a consistent relationship between efficacy and exposure, in distinction to drug dose, has been observed for many of these agents, such that higher trough drug concentrations are associated with greater efficacy. Differences in drug clearance may be an important explanation for this observation. Therefore, a better understanding of the determinants of clearance for therapeutic antibodies may result in optimization of drug regimens.

In previous studies, single-dose pharmacokinetics, pharmacodynamics ($\alpha_4\beta_7$ receptor saturation), safety, and tolerability of vedolizumab were investigated over a dose range of 0.2 to 10 mg/kg in healthy volunteers (intravenous [IV] infusion) (unpublished data). After reaching peak concentrations, vedolizumab serum concentrations fell in a generally biexponential fashion until concentrations reached approximately 1 to 10 ng/mL. Thereafter, concentrations appeared to fall in a nonlinear fashion. The multiple-dose pharmacokinetics and pharmacodynamics of vedolizumab have been investigated following IV infusions of 0.5 and 2 mg/kg in patients with CD and infusion of 2, 6, and 10 mg/kg in patients with UC. Vedolizumab pharmacokinetics was generally linear following an IV infusion over the dose range of 2 to 10 mg/kg in patients with UC. After multiple-dose administration, rapid and near complete $\alpha_4\beta_7$ receptor saturation was achieved following the first dose of vedolizumab.

The efficacy and safety of vedolizumab induction and maintenance therapy were demonstrated in patients with UC in the GEMINI 1 trial (ClinicalTrials.gov number, NCT00783718) and in patients with CD in the GEMINI 2 (ClinicalTrials.gov number, NCT00783692) and GEMINI 3 (ClinicalTrials.gov number, NCT01224171) trials. The exposure-response (efficacy) relationships of vedolizumab in patients with UC and CD for induction and maintenance therapy have been presented elsewhere. For example, in the GEMINI 1 trial, of the subjects who failed to respond, 89% had vedolizumab $C_{trough}$ levels <40 µg/mL. Individuals with vedolizumab clearance >0.14 L/day were associated with diminished efficacy outcomes. Given this clearance cut-point and the approved vedolizumab IV dosing regimen, the following vedolizumab exposure targets are examples for use in this method: Week 6 $C_{trough}$>37.1 µg/mL, Week 14 $C_{trough}$>18.4 µg/mL, and steady-state $C_{trough}$>12.7 µg/mL. Improved outcomes may be seen by the administration of higher doses, e.g., induction doses, resulting in greater serum concentrations.

Definitions

As used herein, the "trough" serum concentration of an antibody refers to the concentration just before the next dose.

"Clinical remission" or "remission" as used herein with reference to ulcerative colitis subjects, refers to a complete Mayo score of less than or equal to 2 points and no individual subscore greater than 1 point. Crohn's disease "clinical remission" refers to a Crohn's Disease Activity Index (CDAI) score of 150 points or less. The "Harvey-Bradshaw Index" (HBI) is a simpler version of the CDAI for data collection purposes. It consists of only clinical parameters including general well-being, abdominal pain, number of liquid stools per day, abdominal mass, hematocrit, body weight, medications to control diarrhea and presence of complications, and requires only a single day's worth of diary entries. Magnetic resonance enterography (MREn) is being evaluated as a method to measure remission.

"Endoscopic remission" as used herein, refers to a condition with a low endoscopic score. An example of a method to assess the endoscopic score in ulcerative colitis is flexible sigmoidoscopy. The endoscopic score in ulcerative colitis can be the Mayo subscore. An example of a method to assess the endoscopic score in Crohn's disease is ileocolonoscopy. The endoscopic score in Crohn's disease can be the simple endoscopic score for Crohn's Disease (SES-CD). The SES-CD can include measures such as the size of ulcers, the amount of ulcerated surface, the amount of affected surface and whether and to what extent the alimentary canal is narrowed.

A "clinical response" as used herein with reference to ulcerative colitis subjects refers to a reduction in complete Mayo score of 3 or greater points and 30% from baseline, (or a reduction in partial Mayo score of 2 or greater points and 25% or greater from baseline, if the complete Mayo score was not performed at the visit) with an accompanying decrease in rectal bleeding subscore of 1 or greater points (≥1) or absolute rectal bleeding score of 1 or less point (≤1). A "clinical response" as used herein with reference to Crohn's disease subjects refers to a 70 point or greater decrease in CDAI score from baseline (week 0). The terms "clinical response" and "response" e.g., alone without any adjective, are used interchangeably herein.

A "complete Mayo score" refers to a composite index of 4 disease activity variables (stool frequency, rectal bleeding, findings on sigmoidoscopy, and physician's global assessment), each scored on a scale from 0 to 3 (higher scores indicate greater disease activity).

A "partial Mayo score" refers to a composite index of 3 disease activity variables (stool frequency, rectal bleeding, and physician's global assessment), each scored on a scale from 0 to 3 (higher scores indicate greater disease activity). Partial Mayo score is calculated analogously to the complete Mayo score but excludes the sigmoidoscopy subscore.

"Endoscopic response" as used herein, refers to a percentage decrease in an endoscopic score from baseline (e.g., at screening or just prior to initial dose). In Crohn's disease, endoscopic response can be assessed by a simple endoscopic score for Crohn's Disease (SES-CD).

"Baseline" as used herein describes a value of a parameter which is measured prior to the initial dose of a treatment. It can refer to a measurement of a sample obtained the same day, the day before, during the week before initial treatment, i.e., at a time period before the first dose when little change is expected until after the first dose and values of the measurement obtained after the first dose can be compared to this baseline value to represent the change caused by the dose.

"Mucosal healing" as used herein as used herein with reference to ulcerative colitis subjects, refers to a Mayo endoscopic subscore of less than or equal to 1. In reference to Crohn's disease, "fistula healing" results in closure or elimination of fistulae. In another reference to Crohn's disease, mucosal healing refers to an improvement in the amount or severity of wounding in mucosae, e.g., the digestive tract. For example, mucosal healing can refer to a decrease in the amount, size or severity of one or more than one ulcer in the digestive tract. In another example, mucosal healing refers to a decrease in one or more parameters selected from the group consisting of wall thickness, enhanced bowel wall contrast, mural edema, ulceration and perienteric vascularity. Such mucosal healing can be expressed as an SES-CD score, or a Magnetic Resonance Index of Activity (MaRIA) score. Complete mucosal healing in Crohn's disease includes absence of ulceration.

The "MaRIA score" is the sum of the scores, e.g., as measured by magnetic resonance enterography, of various mucosal healing parameters for each segment of colon and the terminal ileum (e.g., ileum, ascending colon, transverse colon, descending colon, sigmoid, and rectum).

"Corticosteroid (CS)-free remission" as used herein, refers to patients using oral corticosteroids at baseline who have discontinued corticosteroid use and are in clinical remission at week 52.

"European Quality of Life-5 Dimension (EQ-5D) visual analogue scale (VAS)" as used herein, refers to a questionnaire which is a validated (ahrq.gov/rice/eq5dproj.htm, "U.S. Valuation of the EuroQol EQ-SD™ Health States", accessed 8 Aug. 2012, Bastida et al. BMC Gastroenterology 10:26-(2010), Konig et al. European Journal of Gastroenterology & Hepatology 14:1205-1215 (2002)) instrument used to measure general health-related quality of life (HRQOL) in patients and includes five domains—mobility, self-care, usual activities, pain/discomfort, and anxiety/depression. Patients choose the level of health problems they currently have on each item as "None", "Moderate", or "Extreme" and are scored a 1, 2, or 3, respectively. A composite EQ-5D score can be calculated from the individual scores to assess overall HRQOL. The EQ-5D Visual Analog Scale (VAS) score is a self-assigned rating of overall health using a 20 cm visual, vertical scale, with a score of 0 as the worst and 100 as best possible health. The EQ-5D and EQ-5D VAS have been shown in many studies to be valid and reliable instruments for measuring HRQOL in patients with GI diseases. A decrease of ≥0.3 points in the EQ-5D score represents a clinically meaningful improvement in HRQOL for patients. An increase of greater than or equal to 7 points in the EQ-5D VAS score represents a clinically meaningful improvement in HRQOL for patients.

The "Inflammatory Bowel Disease Questionnaire" ((IBDQ) questionnaire" (Irvine Journal of Pediatric Gastroenterology & Nutrition 28:S23-27 (1999)) is used to assess quality of life in adult patients with inflammatory bowel disease, ulcerative colitis, or Crohn's Disease and includes 32 questions on four areas of HRQOL: Bowel Systems (10 questions), Emotional Function (12 questions), Social Function (5 questions), and Systemic Function (5 questions). Patients are asked to recall symptoms and quality of life from the last 2 weeks and rate each item on a 7-point Likert scale (higher scores equate to higher quality of life). A total IBDQ score is calculated by summing the scores from each domain; the total IBDQ score ranges from 32 to 224. An IBDQ total score greater than 170 is characteristic of the health related quality of life (HRQoL) of patients in remission.

As used herein, "induction therapy" is an initial stage of therapy, wherein a patient is administered a relatively intensive dosing regimen of a therapeutic agent. The therapeutic agent, e.g., antibody, is administered in a way that quickly provides an effective amount of the agent suitable for certain purposes, such as inducing immune tolerance to the agent or for inducing a clinical response and ameliorating disease symptoms (see WO 2012/151247 and WO 2012/151248, incorporated herein by reference).

As used herein, "maintenance therapy" is after induction therapy and is administered in a way that continues the response achieved by induction therapy with a stable level of therapeutic agent, e.g., antibody. A maintenance regimen can prevent return of symptoms or relapse of disease, e.g., IBD (see WO 2012/151247 and WO 2012/151248, incorporated herein by reference). A maintenance regimen can provide convenience to the patient, e.g., be a simple dosing regimen or require infrequent trips for treatment.

The cell surface molecule, "$\alpha 4 \beta 7$ integrin," or "$\alpha 4 \beta 7$," is a heterodimer of an $\alpha_4$ chain (CD49D, ITGA4) and a $\beta_7$ chain (ITGB7). Each chain can form a heterodimer with an alternative integrin chain, to form $\alpha_4\beta_1$ or $\alpha_E\beta_7$. Human $\alpha_4$ and $\beta_7$ genes (GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, $\alpha 4 \beta 7$ can exist in either a resting or activated state. Ligands for $\alpha 4 \beta 7$ include vascular cell adhesion molecule (VCAM), fibronectin and mucosal addressin (MAdCAM (e.g., MAdCAM-1)). The $\alpha 4 \beta 7$ integrin mediates lymphocyte trafficking to GI mucosa and gut-associated lymphoid tissue (GALT) through adhesive interaction with mucosal addressin cell adhesion molecule-1 (MAdCAM-1), which is expressed on the endothelium of mesenteric lymph nodes and GI mucosa.

The term "antibody" herein is used in the broadest sense and specifically covers full length monoclonal antibodies, immunoglobulins, polyclonal antibodies, multispecific antibodies (e.g. bispecific antibodies) formed from at least two full length antibodies, e.g., each to a different antigen or epitope, and individual antigen binding fragments, including dAbs, scFv, Fab, F(ab')$_2$, Fab', including human, humanized and antibodies from non-human species and recombinant antigen binding forms such as monobodies and diabodies.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816, 567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

"Antigen binding fragments" of an antibody comprise at least the variable regions of the heavy and/or light chains of an anti-$\alpha 4 \beta 7$ antibody. For example, an antigen binding fragment of vedolizumab comprises amino acid residues 20-131 of the humanized light chain sequence of SEQ ID NO:2. Examples of such antigen binding fragments include Fab fragments, Fab' fragments, scFv and F(ab')$_2$ fragments of a humanized antibody known in the art. Antigen binding fragments of the humanized antibody of the invention can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the $CH_I$ domain and hinge region of the heavy chain. In one aspect, antigen binding fragments inhibit binding of $\alpha 4 \beta 7$ integrin to one or more of its ligands (e.g. the mucosal addressin MAdCAM (e.g., MAdCAM-1), fibronectin).

The terms "Fc receptor" or "FcR" are used to describe a receptor that binds to the Fc region of an antibody. In one aspect, the FcR is a native sequence human FcR. In another aspect, the FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See review in M. Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:33-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and for regulating the persistence of immunoglobulin G (IgG) and albumin in the serum (reviewed by Rath et al., *J. Clin. Immunol.* 33 Suppl 1:S9-17 (2013)).

The term "hypervariable region" when used herein refers to the amino acid residues of an antibody which are responsible for antigen binding and are found in the "variable domain" of each chain. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disease as well as those in which the disease or its recurrence is to be prevented. Hence, the patient to be treated herein may have been diagnosed as having the disease or may be predisposed or susceptible to the disease. The terms "patient" and "subject" are used interchangeably herein.

Treatment of Vedolizumab Non-Responders with Anti-α4β7 Antibodies

In one aspect, the invention relates to a method of treating IBD (e.g., ulcerative colitis) in a vedolizumab non-responder comprising administering to the vedolizumab non-responder an anti-α4β7 antibody described herein in an amount effective to treat IBD, e.g., in humans. The human patient or subject may be an adult (e.g., 18 years or older), an adolescent, or a child. A pharmaceutical composition comprising an anti-α4β7 antibody can be used as described herein for treating IBD in a subject suffering therefrom. In some embodiments, the treatment results in mucosal healing of the IBD, e.g. UC or CD. In some embodiments, the treatment results in clinical response and/or clinical remission of the IBD, e.g. UC or CD. In some embodiments, the result of treatment, for a patient who began treatment while also being treated with a corticosteroid, is clinical remission and discontinuation of corticosteroid treatment. In some embodiments, the result of the treatment occurs by 14 weeks, by 18 weeks, by 22 weeks, by 26 weeks, by 30 weeks, or by 34 weeks of treatment. In some embodiments, the result of the treatment, e.g., the response, is durable, e.g., a clinical response which is sustained over time, e.g., the patient exhibits a clinical response at both weeks 14 and 30 after initiation of treatment.

As used herein, "non-responders," "nonresponders" or "vedolizumab non-responders" are a select subset of patients having IBD (e.g., ulcerative colitis) who have received a first and second induction dose of anti-α4β7 integrin antibody (e.g., vedolizumab) and show signs of non-responsiveness early in therapy, e.g., vedolizumab therapy (e.g., about three or four weeks after the second induction dose). Signs of non-responsiveness may include clinical response measures and/or measures described herein.

In some embodiments, the treatment for non-responsiveness may be identified using an algorithm comprising factors including, but not limited to, antibody concentration and/or antibody clearance. Antibody concentration may be measured in serum obtained from the patient. In further embodiments, factors in the algorithm for identifying treatment for non-responsiveness comprise body weight and/or albumin levels.

The anti-α4β7 antibody can bind to an epitope on the α4 chain (e.g., humanized MAb 21.6 (Bendig et al., U.S. Pat. No. 5,840,299), on the β7 chain (e.g., FIB504 or a humanized derivative (e.g., Fong et al., U.S. Pat. No. 7,528,236)), or to a combinatorial epitope formed by the association of the α4 chain with the β7 chain. In one aspect, the antibody binds a combinatorial epitope on the α4β7 complex, but does not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Combinatorial epitope anti-α4β7 antibodies can bind α4β7 but not bind α4β1, and/or not bind $α_E$β7, for example. In another aspect, the anti-α4β7 antibody binds to the same or substantially the same epitope as the Act-1 antibody (Lazarovits, A. I. et al., *J. Immunol.,* 133(4): 1857-1862 (1984), Schweighoffer et al., *J. Immunol.,* 151(2): 717-729, 1993; Bednarczyk et al., *J. Biol. Chem.,* 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf of Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

In one aspect, the anti-α4β7 antibodies for use in the treatments are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:4, CDR2, SEQ ID NO:5 and CDR3, SEQ ID NO:6) of the mouse Act-1 antibody and suitable human heavy chain framework regions; and also contain a light chain that contains the 3 light chain CDRs (CDR1, SEQ ID NO:7, CDR2, SEQ ID NO:8 and CDR3, SEQ ID NO:9) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In one aspect, the anti-α4β7 antibody is vedolizumab. Vedolizumab (also called MLN0002, ENTYVIO™ or KYNTELES™) is a humanized immunoglobulin (Ig) G1 mAb directed against the human lymphocyte integrin α4β7. Vedolizumab binds the α4β7 integrin, antagonizes its adherence to MAdCAM-1 and as such, impairs the migration of gut homing leukocytes into GI mucosa. Vedolizumab is an integrin receptor antagonist indicated for adult patients with moderately to severely active UC or CD who have had an inadequate response with, lost response to, or were intolerant to a tumor necrosis factor (TNF) blocker or immunomodulator, or had an inadequate response with, were intolerant to, or demonstrated dependence on corticosteroids. For UC, vedolizumab is for inducing and maintaining clinical response, inducing and maintaining clinical remission, improving endoscopic appearance of the mucosa, and/or achieving corticosteroid-free remission. For CD, vedolizumab is for achieving clinical response, achieving clinical remission, and/or achieving corticosteroid-free remission. In some embodiments, corticosteroid-free remission is achieved through a tapering regimen during continued treatment with vedolizumab.

In another aspect, the humanized anti-α4β7 antibody for use in the treatment comprises a heavy chain variable region comprising amino acids 20 to 140 of SEQ ID NO:1, and a light chain variable region comprising amino acids 20 to 131 of SEQ ID NO:2 or amino acids 21 to 132 of SEQ ID NO:3. If desired, a suitable human constant region(s) can be present. For example, the humanized anti-α4β7 antibody can comprise a heavy chain that comprises amino acids 20 to 470 of SEQ ID NO:1 and a light chain comprising amino acids 21 to 239 of SEQ ID NO:3. In another example, the humanized anti-α4β7 antibody can comprise a heavy chain that comprises amino acids 20 to 470 of SEQ ID NO:1 and a light chain comprising amino acids 20 to 238 of SEQ ID NO:2. The humanized light chain of vedolizumab (e.g., Chemical Abstract Service (CAS, American Chemical Society) Registry number 943609-66-3), with two mouse residues switched for human residues, is more human than the light chain of LDP-02, another humanized anti-α4β7 antibody. In addition, LDP-02 has the somewhat hydrophobic, flexible alanine 114 and a hydrophilic site (Aspartate 115) that is replaced in vedolizumab with the slightly hydrophilic hydroxyl-containing threonine 114 and hydrophobic, potentially inward facing valine 115 residue.

Further substitutions to the humanized anti-α4β7 antibody sequence can be, for example, mutations to the heavy and light chain framework regions, such as a mutation of isoleucine to valine on residue 2 of SEQ ID NO:10; a mutation of methionine to valine on residue 4 of SEQ ID NO:10; a mutation of alanine to glycine on residue 24 of SEQ ID NO:11; a mutation of arginine to lysine at residue 38 of SEQ ID NO:11; a mutation of alanine to arginine at residue 40 of SEQ ID NO:11; a mutation of methionine to isoleucine on residue 48 of SEQ ID NO:11; a mutation of isoleucine to leucine on residue 69 of SEQ ID NO:11; a mutation of arginine to valine on residue 71 of SEQ ID NO:11; a mutation of threonine to isoleucine on residue 73 of SEQ ID NO:11; or any combination thereof; and replacement of the heavy chain CDRs with the CDRs (CDR1, SEQ ID NO:4, CDR2, SEQ ID NO:5 and CDR3, SEQ ID NO:6) of the mouse Act-1 antibody; and replacement of the light chain CDRs with the light chain CDRs (CDR1, SEQ ID NO:7, CDR2, SEQ ID NO:8 and CDR3, SEQ ID NO:9) of the mouse Act-1 antibody.

The present invention provides, in a first aspect, a method for treating a non-responder patient having inflammatory bowel disease (IBD) with an anti-α4β7 antibody, e.g., vedolizumab. In this aspect, the method comprises using an algorithm to evaluate multiple factors including, but not limited to, albumin levels, body weight, and α4β7 antibody concentration. In some embodiments, the method comprises selecting for high dose treatment a patient who has low levels of the antibody. In some embodiments, the method comprises selecting for high dose treatment a patient who has high clearance of the antibody. The method comprises measuring the concentration of the anti-α4β7 antibody in a biological sample from the patient, e.g., blood, serum, plasma, stool, bowel fluid, saliva, inflammatory exudate, at a time, e.g., at least one, two, three, four, five, six, seven, eight or nine weeks, after receiving at least one prior dose of the antibody. In some embodiments, measurement of serum concentration of anti-α4β7 antibody may be an indicator of clearance. Clearance may be affected or further illustrated by other parameters, such as pharmacodynamic factors, clinical factors, inflammation or immune response factors, whose measurement may be used in combination with the measurement of anti-α4β7 antibody. An indication of clearance, alone or in combination with measurements of one or more other parameters, may be used to predict response to anti-α4β7 antibody treatment, identify a patient who is not responding to anti-α4β7 antibody treatment, select a patient for further treatment with anti-α4β7 antibody, select a dose or dosing regimen for the patient, or monitor the effectiveness of the anti-α4β7 antibody during treatment. Low amounts of anti-α4β7 antibody in the patient, e.g., at the time of sampling, indicate that a higher third and optionally high subsequent dosing with anti-α4β7 antibody will provide benefit in the treatment of IBD. A non-responder who has low concentration of the anti-α4β7 antibody may be characterized, a) by a rate of antibody, e.g, vedolizumab, clearance that is greater than about 0.10 L/day, greater than 0.14 L/day, between 0.14 to 0.24 L/day, greater than 0.15 L/day or greater than 0.2 L/day; and/or b) by a serum concentration, e.g., steady state trough concentration, of antibody, e.g., vedolizumab, that is less than 15 µg per ml, less than 14 µg per ml, less than 13 µg per ml, less than 12 µg per ml, less than 10 µg per ml, less than 9 µg per ml, less than 8 µg per ml, less than 7 µg per ml, less than 6 µg per ml, or less than 4 µg per ml or has a range of 1-15 µg per ml, 2-14 µg per ml, 3-13 µg per ml, 1-12 µg/ml, 4-12 µg per ml, 1-11 µg/ml, 1-9 µg/ml, or 5-10 µg ml.

The present invention provides, in a second aspect, a method for treating a non-responder patient having inflammatory bowel disease (IBD) with an anti-α4β7 antibody, e.g., vedolizumab. In this aspect, the method comprises treating the patient with two doses of 300 mg of the anti-α4β7 antibody, the second dose two weeks after the first, measuring the anti-α4β7 antibody concentration five weeks after the first dose and obtaining a clinical response measurement, e.g., a partial Mayo score, six weeks after the first dose of anti-α4β7 antibody. In some embodiments, a non-responder is identified as having a five week anti-α4β7 antibody serum concentration <50 µg/mL and does not meet the criteria, e.g., by partial Mayo score, for clinical response by week six. In some embodiments, the method comprises selecting for high dose treatment a patient who has low levels of the antibody at the five week measurement and does not meet the criteria for clinical response, e.g., by partial Mayo score, at the six week assessment. In some embodiments, a higher dose of vedolizumab is 450 mg or 600 mg, e.g., if administered intravenously, and further may be at a frequency of every four weeks. In other embodiments, a high dose of vedolizumab is a subcutaneous dose of 160 mg, 216 mg, 320 mg, and further may be at a frequency of every week or every two weeks.

In one embodiment, the method for treating IBD in a vedolizumab non-responder with an anti-α4β7 antibody, e.g., vedolizumab, comprises the steps of selecting a human patient having IBD from a group of two or more patients having or suffering from IBD that has, at a time point of three or four weeks after receiving a second dose of vedolizumab, where the first dose of vedolizumab was administered to the subject two weeks prior to the second dose, a serum concentration of no more than about 15, about 14, about 13, about 12, about 11, about 10, about 9, about 8, about 7, or about 6 µg per ml. Specifically, the patient's serum concentration may be between about 1-15, about 2-14, about 3-13, about 4-12, about 1-11, about 1-9 or about 5-10 µg per ml. The patient's serum concentration, e.g., a trough serum concentration, may be less than 12.7 µg/ml, less than 12 µg/ml, or less than 11 µg/ml. In some embodiments, the patient received the prior dose of vedolizumab about two weeks, about three weeks, about four weeks, about five weeks, about six, about seven, about eight or about nine weeks prior to the sampling for serum vedolizumab measurement. Once such a patient is selected from a group of patients, he or she is administered vedolizumab to treat the IBD.

In another aspect, the present invention provides a method for treating IBD in a vedolizumab non-responder with a higher dose (e.g., 600 mg) of an anti-α4β7 antibody, e.g., vedolizumab, than an induction dose (e.g., 300 mg). In some embodiments, the method using vedolizumab comprises the steps of administering three or more doses of vedolizumab to a patient suffering from IBD, wherein the second dose is administered about two weeks after the first dose is administered to the patient; waiting a period of time of at least two weeks, at least three weeks, about four weeks or five weeks; measuring the patient's serum concentration of anti-α4β7 antibody, e.g., vedolizumab; and administering one or more further higher doses (e.g., 600 mg) of vedolizumab to the patient if the patient's serum concentration of anti-α4β7 antibody is less than about 15, about 14, about 13, about 12, about 11, about 10, about 9, about 8, about 7, or about 6 µg per ml. The patient's serum concentration may be between about 1-15, about 2-14, about 3-13, about 4-12, about 1-11, about 1-9, or about 5-10 µg per ml. The patient's serum concentration, e.g., a trough serum concentration of anti-α4β7 antibody may be less than 12.7 µg/ml, less than 12 µg/ml, or less than 11 µg/ml.

The method may further comprise a second measurement of the serum concentration of anti-α4β7 antibody, e.g., vedolizumab, after the third or fourth dose, e.g., about 11 weeks, about 12 weeks, about 13 weeks or about 14 weeks after the first induction dose and continuing treatment at the higher dose (e.g., 600 mg) if the patient's serum concentration is less than about 15, about 14, about 13, about 12, about 11, about 10, about 9, about 8, about 7, or about 6 µg per ml. The patient's serum concentration may be between about 1-15, about 2-14, about 3-13, about 4-12, about 1-11, about 1-9, or about 5-10 µg per ml. The patient's serum concentration, e.g., a trough serum concentration, may be less than 12.7 µg/ml, less than 12 µg/ml, or less than 11 µg/ml.

In some embodiments, the vedolizumab non-responder received the last prior dose, e.g., the second dose, of vedolizumab about three or four weeks prior to the sampling for serum vedolizumab measurement. In other embodiments, the vedolizumab non-responder received the last prior dose three to eight weeks prior to the sampling for serum vedolizumab measurement.

Alternatively, the present invention provides a method of identifying a non-responder for treatment with high dose anti-α4β7 antibody, e.g., vedolizumab, comprising the steps of measuring the concentration of vedolizumab in a sample of serum obtained from a patient suffering from IBD and who received at least one dose of vedolizumab within the previous one or two months, and identifying the patient for continued treatment with high dose vedolizumab if the serum concentration in the sample is less than about 15, about 14, about 13, about 12, about 11, about 10, about 9, about 7, about 6, or about 5 µg per ml. The patient's serum concentration may be between about 1-15, about 2-14, about 3-13, about 4-12, about 1-11, about 1-9, or about 5-10 µg per ml. The patient's serum concentration, e.g., a trough serum concentration, may be less than 12.7 µg/ml, less than 12 µg/ml, or less than 11 µg/ml. In some embodiments, the vedolizumab non-responder received the prior dose of vedolizumab about two weeks, about three weeks, about four weeks, about five weeks or about six weeks prior to the sampling for serum vedolizumab measurement.

Alternatively, at least one dose of the anti-α4β7 antibody, e.g., vedolizumab may be administered to a vedolizumab non-responder, waiting at least about two weeks, or optionally, a period of two to five weeks, and then measuring the patient's serum concentration of vedolizumab and administering one or more further doses of higher dose (e.g., 600 mg) vedolizumab to the patient if the patient's serum concentration is less than about 15, about 14, about 13, about 12, about 11, about 10, about 9, about 8, about 7, or about 6 μg per ml. The patient's serum concentration may be between about 1-15, about 2-14, about 3-13, about 4-12, or about 5-10 μg per ml. The patient's serum concentration, e.g., a trough serum concentration, may be less than 12.7 μg/ml, less than 12 μg/ml, or less than 11 μg/ml.

Alternatively, at least one dose or two doses (e.g., 300 mg) of the anti-α4β7 antibody, e.g., vedolizumab may be administered to a vedolizumab non-responder, waiting at least about five weeks after the first dose of the anti-α4β7 antibody, or optionally, a period of two to five weeks, and then measuring the patient's serum concentration of vedolizumab and administering one or more further doses of higher dose (e.g., 600 mg) vedolizumab to the patient if the patient's serum concentration of anti-α4β7 antibody is less than about 50, about 45, about 40, about 35, about 30, about 35, about 20, or about 15 μg per ml. The patient's serum concentration of anti-α4β7 antibody may be between about 0-50, about 5-50, about 15-50, about 20-50, about 30-50, about 40-50, or about 45-50 μg per ml. The patient's serum concentration of anti-α4β7 antibody may be less than 50 μg/ml, less than 45 μg/ml, or less than 40 μg/ml. The patient's serum concentration of anti-α4β7 antibody may be below 30 μg/ml. Further in this embodiment, the patient may be determined to be a non-responder at week 6 by failure to meet clinical response criteria, e.g., partial Mayo score.

In some embodiments, if further measurement of the serum concentration of anti-α4β7 antibody, e.g., vedolizumab, after the third or fourth dose, e.g., about 11 weeks, about 12 weeks, about 13 weeks, or about 14 weeks after the first induction dose and one or more administrations of the antibody at the higher dose (e.g., 600 mg) finds the patient's serum concentration as more than about 12, about 13, about 14, about 15, about 16, about 17, or about 18 μg per ml, dosing of the patient may return to the induction dose, e.g., 300 mg. The patient's serum concentration may be between about 12-25, about 15-17, about 17-25, about 12-40, about 13-60, about 13-90, or about 15-50 μg per ml. The patient's serum concentration, e.g., a trough serum concentration, may be more than 12.7 μg/ml, more than 13 μg/ml, or more than 14 μg/ml.

Vedolizumab may be administered by any suitable method, such as by one or more of intravenous injection, subcutaneous injection, or infusion. In some embodiments, vedolizumab is administered at a dose of 50 mg, 100 mg, 180 mg, 300 mg, or 600 mg. In some embodiments, the vedolizumab is administered, for example subcutaneously, at a dose of 0.5 mg/kg, 1.0 mg/kg, 1.5 mg/kg, 2.0 mg/kg, 2.5 mg/kg, 3.0 mg/kg. 4.0 mg/kg, or 5.0 mg/kg, at a dose of 108 mg, 216 mg, 160 mg, 165 mg, 320 mg, or 480 mg.

The vedolizumab may be administered once per day, per week, per month, or per year. A vedolizumab dosing regimen may have an initial or induction phase and a maintenance phase. An induction phase may be one or more than one, e.g., two, three or four doses, of high amounts or without long times, such as only one week, two weeks, three weeks or four weeks between each dose. For example, an induction regimen may have two doses, one at day (week) zero and one at week 2 (day 14). A maintenance phase, e.g., to maintain remission of the IBD, may have lower doses or doses further apart than in the induction phase. In some embodiments, the vedolizumab is administered at zero, two and six weeks (induction), and then every four weeks or every eight weeks thereafter (maintenance). Patients with IBD refractory to other therapies may need longer induction periods, e.g., 8, 10 or 12 weeks, before beginning maintenance therapy. In an embodiment, vedolizumab is administered intravenously at zero, two and six weeks, then every eight weeks thereafter. In some embodiments, vedolizumab is administered one or more times, and then at least one month, at least six months, or at least one year later, vedolizumab is again administered one or more times. In some embodiments, 300 mg vedolizumab may be administered by intravenous infusion at zero and two weeks, and then at six weeks, and four weeks intervals or eight week intervals thereafter 600 mg of vedolizumab may be administered intravenously. In some embodiments, 300 mg vedolizumab may be administered by intravenous infusion at zero and two weeks, and then at six weeks 600 mg vedolizumab may be administered by intravenous infusion, and then at four week intervals or eight week intervals thereafter 300 mg of vedolizumab may be administered intravenously. In this embodiment, the patient may have more than or equal to 30 μg/mL (≥30 μg/ml), but less than 50 μg/ml (<50 μg/ml) vedolizumab at the week 5 measurement. In some embodiments, 300 mg vedolizumab may be administered by intravenous infusion at zero and two weeks, and then 600 mg at six weeks and at four week or eight week intervals thereafter until a serum concentration measurement finds more than 12.7 μg/ml, more than 13 μg/ml, more than 14 μg/ml, or the week 13 serum concentration is more than 90 μg/mL vedolizumab, at which time then 300 mg may be administered by intravenous infusion at four week intervals or eight week intervals thereafter. In this embodiment, the patient may have less than 30 μg/ml (<30 μg/ml) vedolizumab at the week 5 measurement. In some embodiments, a patient who is being administered 300 mg vedolizumab every four weeks has a one-week prior-to-the-next-dose measurement of more than 90 μg/mL vedolizumab, the next and subsequent doses may be administered at eight week intervals. In some embodiments, 300 mg vedolizumab may be administered by intravenous infusion at zero and two weeks, 600 mg vedolizumab may be administered by intravenous infusion at six weeks, and then at two-, three- or four-week intervals, 108 mg of vedolizumab may be administered subcutaneously. In some embodiments, 300 mg vedolizumab may be administered by intravenous infusion at zero and two weeks, and then 600 mg at six weeks and at four week or eight week intervals thereafter until a serum concentration measurement finds more than 12.7 μg/ml, more than 13 μg/ml, or more than 14 μg/ml vedolizumab, at which time then 108 mg doses may be administered subcutaneously at two-, three- or four-week intervals. Treatment methods using anti-α4β7 integrin antibodies are described in publication nos. U.S. 2005/0095238, WO2012151248 and WO 2012/151247.

The invention also relates to a method for treating a non-responder with anti-α4β7 antibody, e.g., vedolizumab comprising the steps of calculating the clearance of vedolizumab in a biological sample obtained from a patient suffering from IBD and who was administered at least two doses of vedolizumab within the previous four months (e.g., within the previous three months, within the previous two months), and identifying the patient for treatment with vedolizumab if the clearance in the patient is greater than 0.12 L/day, greater than 0.14 L/day, greater than 0.16 L/day, greater than 0.18 L/day, greater than 0.2 L/day, or between 0.14 to 0.24 L/day. The biological sample may be any biological sample, for example, serum, plasma, saliva, urine, or feces. The method may comprise measuring anti-α4β7 antibody, e.g., a trough concentration, e.g., the week 6 trough concentration, the week 14 trough concentration or the steady state trough concentration. Optionally, the method may comprise measurement of an exposure level of anti-α4β7 antibody.

In some embodiments of the methods of treating a patient with an anti-α4β7 antibody, a patient who does not have sufficient serum trough concentration after one or two doses, e.g., has low serum concentration, e.g., below 15 µg/ml, below 13 µg/ml, below 10 µg/ml, below 8 µg/ml, or below 6 µg/ml and/or high clearance, e.g., >0.12 L/day, >0.14 L/day, >0.16 L/day, or >0.20 L/day after induction, e.g., within two months (e.g., by week 5 or week 6) after the first dose, may modify the standard treatment regimen. In an embodiment, a patient needing a modified regimen has a serum concentration of anti-α4β7 antibody below 13 µg/ml and/or a rate of clearance of the anti-α4β7 antibody >0.14 L/day and/or an albumin concentration of less than 3.2 g/dL. In another embodiment, a patient needing a modified regimen has a serum concentration of anti-α4β7 antibody <50 µg/mL at week 5 after beginning treatment with the anti-α4β7 antibody. Further to this embodiment, the patient needing a modified regimen does not meet the criteria of clinical response, e.g. by partial Mayo score, at week 6 after beginning treatment with the anti-α4β7 antibody. For example, treatment with an anti-α4β7 antibody may be discontinued, dose administration may be more frequent, e.g., every 4 weeks or every 2 weeks instead of every 8 weeks, dose amount may be increased, e.g., from 300 mg to 600 mg. In some embodiments, both frequency and amounts of doses are increased in such patients (e.g., increasing the dose (e.g., to 600 mg) and the frequency (e.g., to treatment every 4 weeks).

The method of treating a patient who is an anti-α4β7 antibody, e.g., vedolizumab, non-responder may further comprise measuring albumin concentration. In therapeutic antibody therapy, this can be a reflection of clearance activity, such as ability to bind the neonate FcR. Alternatively, this can be a reflection of the amount of inflammation being experienced by the patient. For example, blood plasma proteins may be exiting the bloodstream through vessels that are leaky from the IBD inflammation burden. The albumin concentration may be measured prior to treatment with the anti-α4β7 antibody, e.g., vedolizumab, i.e., a baseline measurement. In other embodiments, the albumin concentration may be measured after treatment with the anti-α4β7 antibody, e.g., vedolizumab. In cases of low serum albumin levels, the anti-α4β7 antibody can have a high clearance. Consequently, a patient with low serum albumin levels may not respond to the 300 mg dose or may take longer to respond to treatment with anti-α4β7 antibody. An albumin concentration less than about 3.5 g/dL, about 3.2 g/dL, about 3.0 g/dL, about 2.7 g/dL, or about 2.0 g/dL, or in the range of 2.0 to 3.1 g/dL, in the range of 1.5 to 3.1 g/dL, in the range of 0.8 to 3.1 g/dL or in the range of 0.1 to 3.1 g/dL may further identify the patient for continued treatment with the anti-α4β7 antibody, e.g., vedolizumab e.g., at a higher doses than the induction dose, e.g., 600 mg rather than 300 mg.

The method may further comprise measurement of patient body weight. Body weight may be determined prior to treatment with the anti-α4β7 antibody, e.g., vedolizumab, i.e., at baseline, or may be measured at other times during treatment, e.g., when monitoring patient response. The method may comprise measuring baseline albumin concentration and patient weight. A high weight patient, e.g., greater than 90 kg, greater than 100 kg, greater than 110 kg, or greater than 120 kg, with low albumin levels, e.g., less than 3.2 g/dL, less than 3.0 g/dL, less than 2.5 g/dL or less than 1.2 g/dL, may have high anti-α4β7 antibody clearance and thus may not respond to therapy with the anti-α4β7 antibody or may need a higher or more frequent dose of the anti-α4β7 antibody for continued treatment.

Clearance, e.g., linear clearance, e.g., the volume of blood which is cleared of drug per unit time, may be calculated/estimated/derived by any appropriate means known to those skilled in the art. For example, clearance may be estimated by population approach, such as the model described in PCT/US15/00476. Calculation of clearance can use a model described in the following equation:

$$MAdCAM - 1 = E_0 * \left(1 - \frac{E_{max} * Conc^\gamma}{EC_{50} + Conc^\gamma}\right)$$

where $E_0$ is the baseline MAdCAM-1 percent binding, Emax is the maximum effect, Conc is the vedolizumab serum concentration, $EC_{50}$ is the vedolizumab serum concentration at half-maximum effect, and γ is the Hill-coefficient or slope factor. Parameters for the calculation may include Baseline MAdCAM-1 inhibition (E0) of 12.1%, Concentration at half maximum effect (EC50) of 0.093 µg/mL, Maximum effect (Emax) of 0.959, Hill-coefficient or slope factor (γ) of 0.801 and Exponential residual error variance (σ2exp) of 0.613 (% CV=78.3).

The anti-α4β7 antibody exposure metric, such as trough serum concentration, e.g., serum concentration of anti-α4β7 antibody prior, e.g., 1 day, 2 days, 3 days, 4 days or up to a week prior, to administering a new dose, peak serum concentration, average serum concentration measured at more than one sampling or area under the concentration time curve, is inputted into the model to determine clearance.

The method for identifying a patient for continued treatment with vedolizumab comprising the steps of measuring the clearance of vedolizumab in a biological sample obtained from a patient suffering from IBD can be performed on a patient who was administered at least one dose of vedolizumab within the previous one or two months, and identifying the patient for continued treatment with higher dose vedolizumab if the clearance in the patient is greater than 0.25 L/day, greater than 0.14 L/day, between 0.14 to 0.24 L/day, greater than 0.14 L/day or greater than 0.2 L/day. The biological sample may be any biological sample, for example, serum, plasma, saliva, urine, or feces.

A method of treating a patient who is an anti-α4β7 antibody, e.g., vedolizumab, non-responder may comprise identifying a dose using a combination of measurements.

The combination of measurements may use a calculation, such as a Bayesian calculation method, e.g., the full Bayesian method, e.g., Markov Chain Monte Carlo (MCMC) method or Maximum a-posteriori (MAP) method. One method of devising a dose for a non-responder, e.g., a patient who lacks response after two doses of an anti-α4β7 antibody, e.g., vedolizumab, using linear clearance, such as estimated from antibody serum concentration in a calculation using a population pharmacokinetic model, is described in the Examples. In some embodiments, the calculation, e.g., the Bayesian method, comprises a combination of measurements, such as one, two or all measurements selected from the group consisting of serum albumin level, body weight and anti-α4β7 antibody, e.g., vedolizumab clearance. In some embodiments, the serum albumin level and body weight are measured at baseline, e.g., before treatment with the antibody. In some embodiments, the antibody clearance is calculated from the serum concentration of antibody after induction therapy with the antibody. In other embodiments, the antibody clearance is calculated from the serum concentration of antibody after at least one high dose (e.g., 600 mg) of therapy with the antibody.

In one aspect, the present invention provides a method for treating IBD, e.g., ulcerative colitis, in an anti-α4β7 antibody, e.g., vedolizumab, non-responder with a higher dose (e.g., 600 mg) of an anti-α4β7 antibody, e.g., vedolizumab, than an induction dose (e.g., 300 mg). In some embodiments, the method using vedolizumab comprises the steps of measuring serum albumin and body weight of the patient, administering two or more doses of vedolizumab to a patient suffering from IBD, wherein the second dose is administered about two weeks after the first dose is administered to the patient; waiting a period of time of at least two weeks, at least three weeks, about four weeks or five weeks; measuring the patient's serum concentration of anti-α4β7 antibody, e.g., vedolizumab; combining the results of the measurements of albumin levels, body weight and antibody clearance, and administering one or more further higher doses (e.g., 600 mg) of vedolizumab to the patient if the combination of measurements indicates that the non-responder would benefit from the higher dose. In some embodiments the patient would benefit from the higher dose, e.g., if the higher dose inputted into the method results in a target serum concentration of >12.7 μg/ml, e.g., at steady state. In some embodiments, the patient would benefit from the higher dose if the higher dose inputted into the method results in a target serum concentration of >37.1 μg/ml, e.g., at week 6 after beginning treatment with the antibody. In some embodiments, the higher dose is administered at four-week intervals. In some embodiments, the higher dose is administered at eight-week intervals.

The method may further comprise a second measurement of the serum concentration of anti-α4β7 antibody, e.g., vedolizumab, after the third or fourth dose, e.g., about 11 weeks, about 12 weeks, about 13 weeks or about 14 weeks after the first induction dose and continuing treatment at the higher dose (e.g., 600 mg) if the patient would benefit from the higher dose, e.g., if the higher dose inputted into the method results in a target serum concentration of >12.7 μg/ml, e.g., at steady state. In some embodiments the patient would benefit from the higher dose if the higher dose inputted into the method results in a target serum concentration of >18.4 μg/ml, e.g., at week 14 after beginning treatment with the antibody, e.g., after three or four doses of the antibody. In some embodiments, the higher dose is administered at four-week intervals. In some embodiments, the higher dose is administered at eight-week intervals.

The method may further comprise measuring an endoscopic subscore. Anti-α4β7 antibody, e.g., vedolizumab treatment may be continued with an endoscopic subscore of less than about 3, less than about 2.5, less than about 2, between about 0-2, or less than or equal to 1.

Fecal levels of calprotectin, a neutrophil cytosolic protein, correlate with endoscopic activity in ulcerative colitis. Typically, a non-diseased subject will have a fecal calprotectin level of less than 50 μg/g. A fecal calprotectin level greater than 50 but less than 150 μg/g may be a sign of possible mucosal inflammation, whereas fecal calprotectin levels greater than 150 μg/g is usually a sign of active inflammation. The methods described herein may further comprise measuring the fecal calprotectin concentration. Higher levels of fecal calprotectin are associated with a greater risk of relapse. Vedolizumab treatment may be continued with a fecal calprotectin concentration of less than 1500 μg/g, less 1250 μg/g, less than 1000 μg/g, less than 750 μg/g, less than 500 μg/g, less than 400 μg/g, less than 300 μg/g, less than 250 μg/g, between 200-1200 μg/g, between 350 to 800 μg/g, between 300-1000 μg/g, <50 μg/g, <100 μg/g, <150 μg/g, <200 μg/g, ≤250-499 μg/g, or between 500 to 900 μg/g. Alternatively, fecal calprotectin may be reduced to less than about 50%, 45%, 40%, 35%, 30%, 25%, 20%, between 10-55%, between 10-30%, between 15-35%, between 15-45% or between 20-40% of the baseline or concentration before treatment. Fecal calprotectin in a stool sample can be measured using the PHICAL test kit (Calpro, Lysaker Norway).

The therapy may further comprise a corticosteroid tapering regimen, such as beginning about 1 to 3 weeks or about two weeks, but no more than 10 weeks after starting therapy with the anti-α4β7 antibody, e.g., vedolizumab. In some embodiments, a non-responder IBD patient may be undergoing prior therapy with corticosteroids, such as prednisone, e.g. 10 to 20 mg/day, 20 to 40 mg/day, 25 to 35 mg/day or about 30 mg/day, or budesonide, e.g., 2 to 12 mg/day, 3 to 10 mg/day or about 9 mg/day, at diagnosis or at Baseline. For prednisone, the dose may be reduced at a rate of 5 mg/week until 10 mg/day is reached; for a dose of less than or equal to 10 mg/day, the dose of prednisone is reduced at a rate of 2.5 mg/week until discontinuation. For budesonide, the dose is reduced at a rate of 3 mg every 2 weeks until discontinuation.

Pharmacokinetic and Pharmacodynamic Assays

The anti-α4β7 antibody, e.g., vedolizumab, concentration may be measured by any appropriate means known by those skilled in the art. The serum concentration of the anti-α4β7 antibody, e.g., vedolizumab may be measured one week prior to the next dose or three weeks after the previous dose. In some embodiments, the measurement is five weeks after the first dose of antibody. In some embodiments, the measurement is 13 weeks after the first dose of antibody. In some embodiments, the measurement is at five weeks and at 13 weeks after the first dose of antibody. In some embodiments, the dose of the antibody is adjusted based on the result of the serum concentration measurement. The dose may be increased, e.g., for a serum concentration of less than 50 μg/ml (<50 μg/ml) or less than 30 μg/m (<30 μg/ml), such as increasing the amount of the dose, e.g., from 300 mg to 600 mg, and/or decreasing the interval between doses, e.g., from eight weeks to four weeks for an intravenous dose. The dose may be decreased, e.g., for a serum concentration greater than or equal to 90 μg/ml (≥90 μg/ml), such as decreasing the dose from 600 mg to 300 mg, and/or by increasing the interval between doses, e.g., from four weeks to eight weeks between doses. The dose adjustment may be made in conjunction with a clinical response, e.g., partial Mayo, assessment one week after the serum concentration measurement. For example, an increased dose may be administered to a patient who is does not meet the clinical response, e.g., partial Mayo, criteria and a decreased dose may be administered to a patient who meets the clinical response, e.g., partial Mayo, criteria from the therapy.

In one aspect, the vedolizumab concentration is measured by a sandwich enzyme-linked immunosorbent assay (ELISA) assay. In another aspect, use of a pharmacodynamic assay, inhibition of MAdCAM-1-Fc binding to α4β7-expressing peripheral blood cells by the anti-α4β7 antibody, e.g., vedolizumab in the blood is used as a measure of the extent of $\alpha_4\beta_7$ saturation by the anti-$\alpha 4\beta 7$ antibody, e.g., vedolizumab.

In an embodiment, the anti-$\alpha 4\beta 7$ antibody amount, e.g., in serum can be measured in a pharmacokinetic assay. An immobilized phase, such as a microtiter plate, vessel or bead is coated with a reagent which specifically binds to the anti-$\alpha 4\beta 7$ antibody. The immobilized reagent is contacted with a patient sample, e.g., serum, which may or may not comprise the anti-$\alpha 4\beta 7$ antibody. After incubation and washing, the anti-$\alpha 4\beta 7$ antibody complexed to the coating reagent is contacted with a reagent which binds to the captured antibody and may be detected, e.g., using a label such as horseradish peroxidase (HRP). The binding reagent may be an anti-human antibody, e.g., polyclonal or monoclonal, which binds to the Fc portion of the anti-$\alpha 4\beta 7$ antibody. Addition of an HRP substrate, such as 3,3',5,5'-tetramethylbenzidine (TMB), can allow signal accumulation, such as color development, that can be measured, e.g., spectrophotographically.

In some embodiments, the coating reagent is an anti-idiotypic antibody which specifically binds to the anti-$\alpha 4\beta 7$ antibody, e.g., its variable region or a portion thereof comprising one or more CDRs, such as heavy chain CDR3, SEQ ID NO:6. The anti-idiotypic anti-$\alpha 4\beta 7$ antibody for use in the assay can be specific for, and thus bind, the $\alpha 4\beta 7$ integrin-binding portion of the anti-$\alpha 4\beta 7$ antibody but is not specific for the Fc portion of the anti-$\alpha 4\beta 7$ antibody and thus does not bind the Fc portion of the anti-$\alpha 4\beta 7$ antibody. The anti-idiotypic anti-$\alpha 4\beta 7$ antibody for use in the assay can be specific for, and thus bind, a variable region of the heavy and/or light chain of anti-$\alpha 4\beta 7$ antibody, e.g., selected from the group consisting of amino acids 20 to 140 of SEQ ID NO:1, amino acids 20 to 131 of SEQ ID NO:2 and amino acids 21 to 132 of SEQ ID NO:3. The anti-idiotypic anti-$\alpha 4\beta 7$ antibody for use in the assay can be specific for, and thus bind, an antigen-binding fragment of the anti-$\alpha 4\beta 7$ antibody. The anti-idiotypic antibody can be isolated from an immunization process using the anti-$\alpha 4\beta 7$ antibody or an $\alpha 4\beta 7$ integrin-binding portion thereof, such as an antibody fragment comprising one or more CDRs, and used as isolated or produced by a recombinant method. In some embodiments, the anti-idiotypic anti-$\alpha 4\beta 7$ antibody is raised against an immunogen comprising heavy chain CDR3, SEQ ID NO:6. In other embodiments, the anti-idiotypic anti-$\alpha 4\beta 7$ antibody is raised against an immunogen comprising a variable region of the heavy and/or light chain of anti-$\alpha 4\beta 7$ antibody, e.g., selected from the group consisting of amino acids 20 to 140 of SEQ ID NO:1, amino acids 20 to 131 of SEQ ID NO:2 and amino acids 21 to 132 of SEQ ID NO:3. In some embodiments, the anti-idiotypic antibody is a monoclonal antibody. In some embodiments, an scFv fragment of the anti-idiotypic antibody is used in the assay. In other embodiments, the intact anti-idiotypic antibody is used in the assay.

Generation of an anti-idiotypic anti-$\alpha 4\beta 7$ antibody can proceed in the following general methods. Immunization of a suitable animal (e.g., mouse, rat, rabbit or sheep) with protein, e.g., anti-$\alpha 4\beta 7$ antibody or an $\alpha 4\beta 7$ integrin binding portion thereof, or fusion protein comprising the portion, can be performed with the immunogen prepared for injection in a manner to induce a response, e.g., with adjuvant, e.g., complete Freund's adjuvant. Other suitable adjuvants include TITERMAX GOLD® adjuvant (CYTRX Corporation, Los Angeles, Calif.) and alum. Small peptide immunogens, such as a fragment comprising a CDR, such as CDR3 of the heavy chain can be linked to a larger molecule, such as keyhole limpet hemocyanin. Mice can be injected in a number of manners, e.g., subcutaneous, intravenous or intramuscular at a number of sites, e.g., in the peritoneum (i.p.), base of the tail, or foot pad, or a combination of sites, e.g., i.p. and base of tail. Booster injections can include the same or a different immunogen and can additionally include adjuvant, e.g., incomplete Freund's adjuvant. Generally, where a monoclonal antibody is desired, a hybridoma is produced by fusing a suitable cell from an immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of animals immunized with the antigen of interest. Cells that produce antibodies can be produced using suitable methods, for example, fusion of a human antibody-producing cell and a heteromyeloma or trioma, or immortalization of an activated human B cell via infection with Epstein Barr virus. (See, e.g., U.S. Pat. No. 6,197,582 (Trakht); Niedbala et al., *Hybridoma*, 17:299-304 (1998); Zanella et al., *J Immunol Methods*, 156:205-215 (1992); Gustafsson et al., *Hum Antibodies Hybridomas*, 2:26-32 (1991).) The fused or immortalized antibody-producing cells (hybridomas) can be isolated using selective culture conditions, and cloned by limiting dilution. Cells which produce antibodies with the desired specificity can be identified using a suitable assay (e.g., ELISA (e.g., with immunogen immobilized on the microtiter well).

The anti-$\alpha 4\beta 7$ antibody or the anti-idiotypic anti-$\alpha 4\beta 7$ antibody may be produced by expression of nucleic acid sequences encoding each chain in living cells, e.g., cells in culture. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an anti-$\alpha 4\beta 7$ antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the E. coli expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety. In an insect system, *Autographa californica* nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In other embodiments, the coating reagent is a ligand of the antibody, such as MAdCAM or an $\alpha 4\beta 7$ integrin-binding fragment thereof or fusion protein comprising an $\alpha 4\beta 7$-integrin binding fragment of MAdCAM fused with a non-MAdCAM protein, such as an immunoglobulin G constant domain. Examples of MAdCAM reagents and fusion proteins are described in PCT publication WO9624673 and U.S. Pat. No. 7,803,904, the entire teachings of which are incorporated herein by reference.

HAHA Assay

The human anti-anti-$\alpha 4\beta 7$ antibody activity (HAHA) can be determined by detecting and/or measuring anti-drug antibodies (ADAs) or antibodies specific to the anti-$\alpha 4\beta 7$ antibody (anti-vedolizumab antibodies). There are a number of options, for example, using a screening and titration assay, a confirmation assay, and a neutralizing assay. Serum samples can be measured first in the screening sample at dilutions, for example, 1:5 and 1:50. Positive samples can be confirmed for specificity, titered, and examined for the ability to neutralize anti-$\alpha 4\beta 7$ antibody, e.g., vedolizumab activity.

A screening assay can use a bridging ELISA in which the plate is coated with the anti-$\alpha 4\beta 7$ antibody. The immobilized anti-$\alpha 4\beta 7$ antibody captures the ADA in the test sample which is bound by an anti-$\alpha 4\beta 7$ antibody conjugated to biotin, which is tagged by horseradish peroxidase (HRP)-labeled streptavidin, then detected with an enzymatic substrate, such as TMB. A positive color development, e.g., as measured in a microplate reader, such as Spectramax, with analytical software, such as SOFTMAX Pro3.1.2, indicates the presence of ADAs in the sample. The assay cut point, e.g., in biotin-avidin-HRP based bridging assay, can be determined by using normal human serum samples as negative controls. The mean absorbance values of the 10 negative control serums can be added to 1.65 times the standard deviation of the negative controls to determine the cut point. Thus, the cut point can allow for approximately a 5% false positive rate. In the presence of 1 µg/mL vedolizumab, low titer responses are interfered with such that they may become undetectable, although high levels of immunogenicity are detectable at vedolizumab concentrations greater than 1 µg/mL. For example, while the standard assay sensitivity can be 0.44 ng/ml, in the presence of 0.5 µg/ml vedolizumab, the sensitivity of the assay can be 180 ng/ml.

For these reasons, serum samples can be taken greater than 4 weeks, greater than 8 weeks, greater than 12 weeks or greater than 16 weeks after the final dose of anti-$\alpha 4\beta 7$ antibody. With a longer time period between the prior dose and the sampling, serum drug levels typically can be below the interference level.

Another assay method uses streptavidin coated plates, biotin-labeled anti-$\alpha 4\beta 7$ antibody anchored to streptavidin coated vessels, beads or microtiter plates for the immobilized side of the bridge and heavy metal, such as ruthenium, osmium or rhenium-labeled (e.g., via a sulfo tag) anti-$\alpha 4\beta 7$ antibody for the other side of the bridge. The bridged complex can be built on the plate by stepwise additions and washes between or in solution, with both sides of the bridge contacting diluted serum sample, then transferred to the plate. An example of an assay using this method has a sensitivity of 3.90 ng/ml anti-anti-$\alpha 4\beta 7$ antibody. Detection of the heavy metal labeled bridge complex, e.g., a ruthenium-labeled complex, by electrochemiluminescence (ECL), e.g., in a Meso Scale Discovery Sector Imager 6000 (Rockville, Md.), may be more sensitive than an HRP method and/or have higher tolerance to the amount of anti-$\alpha 4\beta 7$ antibody in the serum. Thus there would not be a need to wait for a delayed sample after the serum drug level lowers. In some embodiments, pretreatment of the serum sample with acid, e.g., acetic acid or low pH glycine, to release the anti-$\alpha 4\beta 7$ antibody from the patient-derived anti-anti-$\alpha 4\beta 7$ antibodies prior to contacting with the bridging anti-$\alpha 4\beta 7$ antibodies can reduce the interference from the drug in the serum. For example, while the standard assay sensitivity can be 3.90 ng/ml, in the presence of 5 µg/ml vedolizumab in serum, the sensitivity of the assay can be 10 ng/ml.

In an embodiment, an assay to detect anti-vedolizumab antibodies in a sample of serum from a patient comprises diluting serum by a standard dilution factor, such as 1:5, 1:25, 1:50, and/or 1:125; treating with acetic acid; combining the acid treated diluted sample with an assay composition comprising a high pH reagent, such as high concentration TRIS buffer for neutralizing the acid, a biotin-labeled vedolizumab and a ruthenium-labeled vedolizumab for a time sufficient to form a bridge with serum-derived anti-vedolizumab antibodies between the two tagged versions of vedolizumab; transferring the complexes to a streptavidin-coated plate; washing the plate so only ruthenium complexed by the antibody bridge is present. Detection of the bound ruthenium-labeled complex and measuring the sample by electrochemiluminescence in the microplate reader can be achieved by adding a read solution such as tripropylamine and applying voltage to stimulate the ruthenium label complexed to the plate via the antibody bridge.

After the initial screening assay, samples can be further tested in a confirmatory assay that uses excess unlabeled anti-$\alpha 4\beta 7$ antibody to demonstrate specificity. Confirmed positive samples can be further assessed for the ability of the HAHA to neutralize the binding of the anti-$\alpha 4\beta 7$ antibody, e.g., vedolizumab to cells. A competitive flow cytometry-based assay was designed to determine the ability of the immune serum to inhibit the binding of labeled vedolizumab to an $\alpha_4\beta_7$ integrin-expressing cell line, RPMI8866, and detection by flow cytometry.

The results can indicate categories of immunogenicity status: Negative: no positive HAHA sample; Positive: at least 1 positive HAHA sample; Transiently positive: at least 1 positive HAHA sample and no consecutive positive HAHA samples; and Persistently positive: at least 2 or more consecutive positive HAHA samples. Negative patients are likely to respond to anti-α4β7 antibody and can continue being treated with the antibody. Persistently positive patients are likely to have high clearance of anti-α4β7 antibody and may not respond to anti-α4β7 antibody treatment. Positive patients may have high clearance of anti-α4β7 antibody and may not respond to anti-α4β7 antibody. Positive patients can have an additional serum sample 2, 3, 4, 5 or 6 weeks after another dose of anti-α4β7 antibody to determine if they are persistently positive or transiently positive. Transiently positive patients are likely to respond to anti-α4β7 antibody treatment and treatment of these patients can be continued.

Titers of immunogenicity levels also may be determined. Titer categories include ≥5 (low), ≥50, ≥125, ≥625 and ≥3125 (high). A patient with a high titer in a positive sample may have high clearance of anti-α4β7 antibody and may not respond to anti-α4β7 antibody treatment. A patient with a low titer in a positive sample may respond to anti-α4β7 antibody treatment.

The invention will be more fully understood by reference to the following examples. They should not, however, be construed as limiting the scope of the invention. All literature and patent citations are incorporated herein by reference.

EXEMPLIFICATION

Example 1

Data from a Phase 3 vedolizumab clinical trial (GEMINI I) included week 6 outcomes, Partial Mayo Score (PMS), Clinical Response (CR), and Clinical Remission (RM), individual-specific covariates, and individual-predicted plasma vedolizumab concentrations and clearances based on a prior population pharmacokinetic (PK) analysis (Rosario et al. 2015 *Alimentary Pharmacology & Therapeutics* 42 (2): 188-202). The limited dose-ranging information in this study yielded the potential for confounded causal inference about the exposure-response (E-R) relationship, and therefore, a propensity score based case-matching analysis was conducted.

For each clearance quartile, a logistic propensity score model was fit to the collection of treated subjects and all controls using all measured covariates as predictors. A robust estimate of the standard deviation of the propensity score distribution was then obtained based on the fitted propensity scores.

For each subject in the clearance quartile, a match was randomly selected (with replacement) from the subjects in the control arm within a caliper of 0.2 times the robust estimate of the standard deviation obtained in the previous step. If for a particular treated subject there were no controls within the caliper, the treated subject remained unmatched and was excluded from the outcome analysis.

The previous step was then repeated 1,000 times and for each candidate match, the Absolute Standardized Difference in Means (ASDM) was calculated for all covariate main effects and two-way interactions. The optimal subset of matched controls was then identified as the candidate match with the lowest maximum ASDM among interaction effects that satisfied ASDM <0.2 for all main effects. Given the case-matching results, quartiles of clearance and predicted Week 6 and steady state trough vedolizumab concentrations were compared with outcomes for both unmatched and case-matched data.

RESULTS: Relationships for all exposure metrics and each outcome were evident in the quartile analysis of the raw data, although relationships were more robust for Week 6 PMS and CR endpoints than for RM. After case-matching adjustment for potential confounding, a clear relationship was still evident for the PMS and CR endpoints. Individuals with vedolizumab clearance >0.14 L/day was associated with diminished efficacy outcomes (PMS decrease <2 units, clinical response odds ratio <4). Given this clearance cut-point of 0.14 L/day and the approved vedolizumab IV dosing regimen, a target steady state vedolizumab trough concentration of >12.7 μg/mL was calculated. Simulations with the published population PK model were conducted to evaluate strategies to 1) identify high clearance individuals, and 2) recommend dose adjustments necessary to achieve the steady-state target, both based on Week 5 plasma vedolizumab concentrations in this study.

The estimated E-R relationships will inform the design of future studies evaluating the impact of dose individualization on clinical outcomes in UC patients with high clearance.

Example 2

Methods Implemented in the Dose Calculator Algorithm

The case-matching exposure- and clearance-response analyses provided a target clearance value to identify high-clearance individuals, and target vedolizumab trough concentrations to achieve with future dosing regimens (Week 14 and steady-state).

The dose calculator algorithm was designed to select the best regimen for an individual patient, given input of patient baseline covariates (weight, albumin), vedolizumab dosing history, and observed plasma vedolizumab concentrations at week 5 and week 13. This algorithm is based on a previously defined population pharmacokinetic model (Rosario et al. 2015, *Alimentary Pharmacology & Therapeutics* 42 (2): 188-202.).

The methodology is based on a MAP (maximum a-posteriori) Bayesian estimation method ("Bayesian Analysis—MIT OpenCourseWare," Probabilistic Modeling and Bayesian Analysis, Latham, B. and Rudin, C., MIT course 15.097 notes, 2012), aimed at estimating individual patient clearance, given the inputs described above and the prior population pharmacokinetic model. The algorithm, then applies the individual patient information and clearance estimate to simulate expected outcomes of each of the candidate dosing regimens. The optimal regimen is one which achieves trough concentrations at least equal to the target vedolizumab concentrations, while maximizing the duration of the dosing interval.

Example 3

Effect of Modified Vedolizumab Dose on Treatment Outcomes in Non-responders with Moderately to Severely Active Ulcerative Colitis A phase 4, open-label, multicenter study will be used to investigate the efficacy and safety of modified dosing of vedolizumab IV, compared with standard dosing of vedolizumab IV, over a 30-week treatment period. This study will enroll adult subjects with moderately to severely active ulcerative colitis (UC). Approximately 200 subjects will be enrolled in order to randomize up to 100 non-responder subjects with high vedolizumab drug clearance.

The study is comprised of a 28-day screening period, a 6-week lead-in period, and a 24-week randomized treatment period, followed by an 18-week follow-up safety visit and a long-term follow-up (LTFU) safety survey by telephone 6 months after the last dose of study drug.

All eligible subjects will receive induction therapy with vedolizumab IV 300 mg on Day 1 and Week 2 (lead-in period). Subjects who are assessed as having high vedolizumab clearance (>0.14 L/day, or based on a predefined Week 5 serum vedolizumab concentration threshold (<50 µg/mL)) at Week 5 and who are non-responders (based on partial Mayo score) at Week 6 will be randomized to receive either standard or modified doses of vedolizumab IV. Subjects who are non-responders based on the partial Mayo score at Week 6 and who are assessed as having high vedolizumab clearance (>0.14 L/day, or meet the <50 µg/mL serum vedolizumab concentration threshold) at Week 5 will proceed with randomization at Week 6 in a 1:1 ratio to receive either dose modified or standard vedolizumab IV therapy. For subjects randomized to the modified dose arm, the Dose Calculator Algorithm may be used to select a regimen.

Vedolizumab IV standard treatment is 300 mg administered every eight weeks (weeks 6, 14, and 22). The Vedolizumab IV modified treatment At week 6, all subjects randomized to the Dose Optimization Arm will be assigned to either Regimen A or Regimen B (below) based on the subject's Week 5 serum vedolizumab concentration. Subjects with serum vedolizumab concentration <50 µg/mL and ≥30 µg/mL will be assigned to Regimen A, and subjects with serum vedolizumab concentration <30 µg/mL will be assigned to Regimen B:

Regimen A: Vedolizumab IV 600 mg (Week 6) and 300 mg Q4W (Weeks 10, 14, 18, 22, and 26), OR Regimen B: Vedolizumab IV 600 mg (Week 6) and 600 mg Q4W (Weeks 10, 14, 18, 22, and 26).

At Week 14 and beyond, dosing will continue as previously scheduled unless the subject's most recent preceding serum vedolizumab concentration is >90 µg/mL (e.g., Week 13 PK sampling prior to Week 14

Alternatively, a patient who is a non-responder by partial Mayo score at week 6 may be administered 600 mg of antibody and the Dose Calculator Algorithm may then be used to select the dose to be administered at Week 10 (e.g., 0, 300, or 600 mg) with the longest interval that will result in the highest probability of achieving the target exposure. At week 14 and beyond, dosing will be based on updated vedolizumab clearance estimates from the week 13 serum vedolizumab concentration, dosing history, and baseline covariate information, using a model-based algorithm to achieve steady state of 12.7 µg/mL. For subjects in the Modified Dose arm, the algorithm will select 1 of the following 4 regimens, based on highest probability of achieving or maintaining the steady state target exposure of 12.7 µg/mL at a frequency with the longest interval:

Vedolizumab IV 300 mg Q8W (Weeks 14 and 33)
Vedolizumab IV 300 mg Q4W (Weeks 14, 18, 22, and 26)
Vedolizumab IV 600 mg Q8W (Weeks 14 and 22)
Vedolizumab IV 600 mg Q4W (Weeks 14, 18, 22, and 26).

The primary objective of the study is to determine the effect of vedolizumab IV dose modification on mucosal healing (Mayo endoscopic subscore <1 point at Week 30) compared with the standard vedolizumab IV dosing regimen at Week 30 in ulcerative colitis subjects with high vedolizumab clearance who are Week 6 non-responders. Secondary endpoints will include:

Proportion of subjects achieving clinical remission, where clinical remission is defined as a complete Mayo score of ≤2 points and no individual subscore >1 point at Week 30.

Proportion of subjects achieving clinical response, where clinical response is defined as a reduction in complete Mayo score of ≥3 points and ≥30% from Baseline (Day 1) with an accompanying decrease in rectal bleeding subscore of ≥1 point or absolute rectal bleeding subscore of ≤1 point, at Week 30.

Proportion of subjects achieving clinical response (based on partial Mayo score), which is defined as a reduction in partial Mayo score of ≥2 points and ≥25% from Baseline with an accompanying decrease in rectal bleeding subscore of ≥1 point or absolute rectal bleeding subscore of ≤1 point at, Week 14.

Proportion of subjects using oral corticosteroids at Baseline who have discontinued corticosteroids and are in clinical remission, at Week 30.

---

The invention claimed is:

1. A method of treating a vedolizumab non-responder having moderately to severely active ulcerative colitis, the method comprising intravenously administering vedolizumab at a dose of 600 mg to the non-responder at week 6 following a first intravenous 300 mg dose of vedolizumab at day 1, wherein the non-responder is a patient having moderately to severely active ulcerative colitis who is characterized as having either a vedolizumab rate of clearance of greater than 0.14 L/day or a serum vedolizumab concentration threshold of less than 50 µg/mL at week 5 following the first dose of vedolizumab, and wherein the non-responder received a second intravenous 300 mg dose of vedolizumab week 2 following the first 300 mg dose at day 1.

2. The method of claim 1, wherein the next dose and subsequent doses of vedolizumab is 300 mg.

3. The method of claim 1, wherein the subsequent doses of vedolizumab are 600 mg and the interval between doses is 2 to 8 weeks.

4. The method of claim 2, wherein the doses are administered at four week intervals.

5. The method of claim 3, wherein the 600 mg doses are administered until clinical response and/or remission is achieved.

6. The method of claim 3, wherein the 600 mg doses are administered until mucosal healing is achieved.

7. The method of claim 3, wherein the 600 mg doses are administered until the trough serum concentration of vedolizumab is >12 µg/ml.

8. The method of claim 3, wherein the 600 mg doses are administered until the serum concentration of vedolizumab is >90 µg/ml.

9. The method of 7, further comprising reducing the dose to 300 mg if the trough serum concentration of vedolizumab is >12 µg/ml or the serum concentration of vedolizumab is >90 µg/ml.

10. The method of claim 4, further comprising reducing the dose to eight week intervals if the trough serum concentration of vedolizumab is >12 µg/ml or the serum concentration of vedolizumab is >90 µg/ml.

11. The method of claim 1, wherein the treatment results in mucosal healing.

12. The method of claim 1, wherein the treatment results in clinical response and/or clinical remission.

13. The method of claim 1, wherein the treatment results in discontinuation of corticosteroid use.

14. The method of claim 1, wherein the patient has had an inadequate response with, lost response to, or intolerance of at least one of immunomodulators, corticosteroids, or TNFα antagonists.

15. A method of treating a vedolizumab non-responder having moderately to severely active ulcerative colitis, the method comprising the steps of:
   a) measuring the concentration of vedolizumab in a human patient having moderately to severely active ulcerative colitis, wherein the patient was administered an induction phase dosing regimen of vedolizumab comprising intravenous administration of a first dose of 300 mg of vedolizumab and a second 300 mg dose of vedolizumab administered two weeks after the first dose, and wherein the concentration or clearance of vedolizumab is measured 5 weeks after the first dose;
   b) selecting the patient whose measurement in step a) indicates either a vedolizumab rate of clearance greater than 0.14 L/day or a serum vedolizumab concentration threshold of less than 50 µg/mL, wherein the selected patient is a vedolizumab non-responder; and
   c) administering 600 mg of vedolizumab to the vedolizumab non-responder 6 weeks after the first dose, thereby treating ulcerative colitis.

16. The method of claim 15, wherein the treatment results in mucosal healing.

17. A method of treating a vedolizumab non-responder suffering from moderately to severely active ulcerative colitis, the method comprising the steps of:
a) intravenously administering two 300 mg doses of vedolizumab to a human patient suffering from moderately to severely active ulcerative colitis, wherein the second dose is administered about two weeks after the first dose is administered to the human patient;
b) selecting a vedolizumab non-responder wherein the vedolizumab non-responder has a vedolizumab rate of clearance greater than 0.14 L/day or a serum vedolizumab concentration threshold of less than 50 µg/mL as determined 5 weeks after the first dose; and
c) administering 600 mg of vedolizumab to the vedolizumab non-responder six weeks after the first dose of vedolizumab, thereby treating the vedolizumab non-responder suffering from moderately to severely active ulcerative colitis.

18. A method of treating a vedolizumab non-responder suffering from moderately to severely active ulcerative colitis, the method comprising the steps of:
a) intravenously administering two 300 mg doses of vedolizumab to a human patient suffering from moderately to severely active ulcerative colitis, wherein the second dose is administered about two weeks after the first dose is administered to the human patient;
b) waiting a period of time of three weeks;
c) measuring the patient's serum concentration of vedolizumab, wherein the patient is a vedolizumab non-responder if the patient has a serum vedolizumab concentration threshold of less than 50 µg per ml and has not achieved a clinical response; and
d) administering one or more 600 mg doses of vedolizumab to the vedolizumab non-responder identified in (c) beginning 6 weeks after the first dose,
such that the vedolizumab non-responder suffering from moderately to severely active ulcerative colitis is treated.

19. The method of claim 18, wherein the patient's serum concentration is 1-13 µg per ml.

20. The method of claim 17, wherein the vedolizumab serum concentration is measured by a sandwich ELISA assay.

21. A method for treating a vedolizumab non-responder, the method comprising administering vedolizumab at a 600 mg dose to a human patient suffering from moderately to severely active ulcerative colitis whose clearance of vedolizumab is greater than 0.14 L/day after being administered two 300 mg doses of vedolizumab within the previous five weeks, wherein the two 300 mg doses are intravenously administered as an initial dose and as a second dose 2 weeks after the initial dose, and wherein the 600 mg dose is administered 6 weeks after the initial dose.

22. The method of claim 21, further comprising measuring anti-vedolizumab antibodies.

23. The method of claim 21, further comprising measuring albumin concentration.

24. The method of claim 23, further comprising measuring body weight.

25. The method of claim 23, wherein the albumin concentration is <3.2 g/dL.

26. A method for treating a vedolizumab non-responder, the method comprising administering vedolizumab at a 600 mg dose to a human patient suffering from IBD whose serum concentration of vedolizumab is <50 µg/ml after being intravenously administered a first dose of 300 mg vedolizumab and a second dose of 300 mg of vedolizumab two weeks after the first dose, wherein the serum concentration of vedolizumab is measured 5 weeks after the first dose and the 600 mg dose is administered 6 weeks after the first dose.

27. The method of claim 26, further comprising obtaining a partial Mayo score one week after the measurement wherein the partial Mayo score does not indicate a clinical response.

28. The method of claim 26, wherein the serum concentration of vedolizumab is >30 µg/ml and <50 µg/ml.

29. The method of claim 26, further comprising a subsequent dose of 300 mg of vedolizumab four weeks after the 600 mg dose.

30. The method of claim 26, further comprising one or more additional doses of 600 mg of vedolizumab at four week intervals.

31. The method of claim 29, further comprising one or more additional doses of 300 mg of vedolizumab at four week intervals.

32. The method of claim 31, further comprising measuring the serum concentration of vedolizumab three weeks after the previous dose.

33. The method of claim 32, further comprising decreasing the dose if the concentration is >90 µg/ml, wherein the 600 mg dose is decreased to 300 mg or wherein the 300 mg dose is administered at eight week intervals.

34. The method of claim 26, further comprising measuring anti-vedolizumab antibodies.

35. The method of claim 34, further comprising measuring albumin concentration.

36. The method of claim 35, further comprising measuring body weight.

37. The method of claim 35, wherein an albumin concentration <3.2 g/dL further identifies the patient for continued treatment with vedolizumab at a higher dose.

38. The method of claim 26, wherein the treatment results in mucosal healing.

39. The method of claim 26, wherein the treatment results in clinical response and/or clinical remission.

40. The method of claim 26, wherein the treatment results in discontinuation of corticosteroid use.

41. The method of claim 26, wherein the patient has had an inadequate response with, lost response to, or intolerance of at least one of immunomodulators, corticosteroids, or TNFα antagonists.

42. The method of claim 3, wherein the doses are administered at four week intervals.

43. The method of claim 4, wherein the 600 mg doses are administered until clinical response and/or remission is achieved.

44. The method of claim 4, wherein the 600 mg doses are administered until mucosal healing is achieved.

* * * * *